US010195264B2

(12) United States Patent
Contorni et al.

(10) Patent No.: US 10,195,264 B2
(45) Date of Patent: *Feb. 5, 2019

(54) IMMUNISING AGAINST MENINGOCOCCAL SEROGROUP Y USING PROTEINS

(75) Inventors: Mario Contorni, Siena (IT); Marzia Giuliani, Siena (IT); Mariagrazia Pizza, Siena (IT)

(73) Assignee: GLAXOSMITHKLINE BIOLOGICALS S.A. (BE)

( * ) Notice: Subject to any disclaimer, the term of this patent is extended or adjusted under 35 U.S.C. 154(b) by 1575 days.

This patent is subject to a terminal disclaimer.

(21) Appl. No.: 11/587,189

(22) PCT Filed: Apr. 22, 2005

(86) PCT No.: PCT/IB2005/001279
§ 371 (c)(1),
(2), (4) Date: Aug. 22, 2007

(87) PCT Pub. No.: WO2005/102384
PCT Pub. Date: Nov. 3, 2005

(65) Prior Publication Data
US 2010/0143418 A1 Jun. 10, 2010

(30) Foreign Application Priority Data

Apr. 22, 2004 (GB) .................................. 0408977.7

(51) Int. Cl.
A61K 39/095 (2006.01)

(52) U.S. Cl.
CPC .................. A61K 39/095 (2013.01)

(58) Field of Classification Search
CPC ...... A61K 39/095; A61K 31/00; A61K 39/00; A61K 39/39; A61K 2039/6068; A61K 2039/55505; A61K 39/116; A61K 38/00; A61K 2300/00; A61K 35/74; C07K 14/22; C07K 14/195; C07K 14/00; C07K 16/1217; G01N 2333/22; G01N 2333/195; C12N 1/00
USPC ......... 424/250.1, 249.1, 184.1, 278.1, 282.1, 424/780; 530/300, 806, 820, 825; 435/4, 435/71.2; 514/1.1
See application file for complete search history.

(56) References Cited

U.S. PATENT DOCUMENTS

| | | | |
|---|---|---|---|
| 4,309,095 A | 1/1982 | Buckley | |
| 4,835,621 A | 5/1989 | Black | |
| 5,020,262 A | 6/1991 | Pena | |
| 5,547,670 A | 8/1996 | Goldstein et al. | |
| 5,887,375 A | 3/1999 | Watson | |
| 6,013,267 A | 1/2000 | Blake et al. | |
| 6,028,049 A | 2/2000 | Jacobs et al. | |
| 6,192,614 B1 | 2/2001 | Cliburn | |
| 6,197,312 B1 | 3/2001 | Peak et al. | |
| 6,425,697 B1 | 7/2002 | Potts et al. | |
| 6,709,660 B1 | 3/2004 | Scarlato et al. | |
| 6,914,131 B1 * | 7/2005 | Scarlato et al. | ............. 536/23.1 |
| 7,348,006 B2 * | 3/2008 | Contorni et al. | .......... 424/184.1 |
| 7,368,261 B1 | 5/2008 | Rappuoli | |
| 7,491,517 B2 * | 2/2009 | Reddy | .............................. 435/72 |
| 7,576,176 B1 * | 8/2009 | Fraser et al. | ................... 530/350 |
| 7,604,810 B2 | 10/2009 | Rappuoli | |
| 7,612,192 B2 * | 11/2009 | Fraser et al. | ................... 536/23.7 |
| 7,655,245 B2 * | 2/2010 | Scarlato et al. | ........... 424/250.1 |
| 7,700,119 B2 * | 4/2010 | Giuliani et al. | ........... 424/250.1 |
| 7,731,967 B2 | 6/2010 | O'Hagan et al. | |
| 7,785,608 B2 | 8/2010 | Zlotnick et al. | |
| 7,803,387 B2 * | 9/2010 | Arico et al. | ................ 424/250.1 |
| 8,101,194 B2 | 1/2012 | Zlotnick et al. | |
| 8,114,960 B2 | 2/2012 | Arico et al. | |
| 8,226,960 B2 | 7/2012 | Masignani et al. | |
| 8,293,251 B2 | 10/2012 | Scarlato et al. | |
| 8,394,390 B2 | 3/2013 | Galeotti et al. | |
| 8,398,988 B2 | 3/2013 | Contorni et al. | |
| 8,398,999 B2 | 3/2013 | Masignani et al. | |
| 8,470,340 B2 | 6/2013 | Beernink et al. | |
| 8,524,251 B2 | 9/2013 | Fraser et al. | |
| 8,563,007 B1 | 10/2013 | Zlotnick et al. | |
| 8,574,597 B2 | 11/2013 | Zlotnick | |
| 8,663,656 B2 | 3/2014 | Pizza | |
| 8,703,914 B2 | 4/2014 | Arico et al. | |
| 8,734,812 B1 | 5/2014 | Galeotti et al. | |
| 8,765,135 B2 * | 7/2014 | Contorni | .............. A61K 39/095 424/185.1 |
| RE45,137 E | 9/2014 | O'Hagan et al. | |
| 8,834,888 B2 | 9/2014 | Contorni et al. | |
| 8,840,907 B2 | 9/2014 | Pizza | |
| 8,968,748 B2 | 3/2015 | Granoff et al. | |

(Continued)

FOREIGN PATENT DOCUMENTS

| | | | |
|---|---|---|---|
| EP | 0273116 A2 | 7/1988 | |
| EP | 0467714 A1 | 1/1992 | |

(Continued)

OTHER PUBLICATIONS

Granoff et al, Vaccine, 2009, 27S:B117-B125.*
Frasch et al, Vaccine, 2009, 27S:B112-B116.*
Comanducci et al, J. Exp. Med., 2002, 195/11:1445-1454.*
Feavers et al, Vaccine, 2009, 27S:B42-B50.*
Holst et al, Vaccine, 2009, 27S:B3-B12.*
Seib et al, Vaccine, 2010, 28:2416-2427.*
Lucidarme et al, J. Clin. Microbiol, 2009, 47/11:3577-3585.*

(Continued)

Primary Examiner — Mary Maille Lyons

(57) ABSTRACT

The invention uses polypeptide antigens and/or OMVs to immunize against serogroups A, C, W135 and Y (and against serogroup Y in particular). Serogroup B polypeptides can achieve this protection, thus permitting a single polypeptide-based vaccine to be used for protecting against all of serogroups A, B, C, W135 and Y.

15 Claims, No Drawings

Specification includes a Sequence Listing.

(56) References Cited

U.S. PATENT DOCUMENTS

| | | | |
|---|---|---|---|
| 8,980,286 | B2 | 3/2015 | Comanducci |
| 9,011,869 | B2 | 4/2015 | Pizza |
| 9,056,075 | B2 | 6/2015 | Pizza |
| 9,067,987 | B2 | 6/2015 | Galeotti et al. |
| 9,139,621 | B2 | 9/2015 | Fraser |
| 9,150,898 | B2 | 10/2015 | Arico |
| 9,156,894 | B2 | 10/2015 | Masignani et al. |
| 9,249,196 | B2 | 2/2016 | Fraser et al. |
| 2002/0160016 | A1 | 10/2002 | Peak et al. |
| 2004/0092711 | A1 | 5/2004 | Arico |
| 2004/0167068 | A1* | 8/2004 | Zlotnick et al. ............ 514/12 |
| 2004/0249125 | A1* | 12/2004 | Pizza et al. ............ 530/350 |
| 2005/0222385 | A1 | 10/2005 | Pizza |
| 2005/0232936 | A1 | 10/2005 | Arico et al. |
| 2006/0051840 | A1 | 3/2006 | Arico et al. |
| 2006/0171957 | A1* | 8/2006 | Pizza ............ 424/190.1 |
| 2006/0240045 | A1 | 10/2006 | Berthet et al. |
| 2006/0251670 | A1 | 11/2006 | Comanducci et al. |
| 2007/0026021 | A1* | 2/2007 | Fraser et al. ............ 424/250.1 |
| 2007/0082014 | A1 | 4/2007 | Costantino |
| 2007/0231342 | A1* | 10/2007 | Giuliani et al. ............ 424/190.1 |
| 2007/0253984 | A1 | 11/2007 | Khandke et al. |
| 2008/0063665 | A1* | 3/2008 | Oster et al. ............ 424/232.1 |
| 2008/0241180 | A1* | 10/2008 | Contorni ............ 424/190.1 |
| 2009/0232820 | A1 | 9/2009 | Fraser et al. |
| 2009/0285845 | A1 | 11/2009 | Masignani et al. |
| 2010/0015151 | A1* | 1/2010 | Rappuoli et al. ............ 424/139.1 |
| 2010/0143418 | A1* | 6/2010 | Contorni et al. ............ 424/250.1 |
| 2010/0267931 | A1 | 10/2010 | Arico et al. |
| 2011/0020390 | A1 | 1/2011 | Pizza et al. |
| 2012/0107339 | A1 | 5/2012 | Granoff et al. |
| 2013/0236489 | A1 | 9/2013 | Serruto et al. |
| 2014/0037668 | A1 | 2/2014 | Giuliani et al. |
| 2014/0363462 | A1 | 12/2014 | Arico et al. |
| 2015/0079124 | A1 | 3/2015 | Fraser et al. |
| 2015/0086582 | A1 | 3/2015 | Fraser et al. |

FOREIGN PATENT DOCUMENTS

| | | | |
|---|---|---|---|
| EP | 1645631 A2 | 4/2006 | |
| EP | 1790660 A2 | 5/2007 | |
| EP | 2351767 A2 | 8/2011 | |
| NL | 8901612 A | 7/1990 | |
| WO | WO-90/06696 A2 | 6/1990 | |
| WO | WO 90/11367 | 10/1990 | |
| WO | WO-92/16643 A1 | 10/1992 | |
| WO | WO-95/33049 A2 | 12/1995 | |
| WO | WO-96/29412 A1 | 9/1996 | |
| WO | WO-97/13860 A1 | 4/1997 | |
| WO | WO-98/17805 A2 | 4/1998 | |
| WO | WO-99/24578 A2 | 5/1999 | |
| WO | WO-99/36544 A2 | 7/1999 | |
| WO | WO-99/57280 A | 11/1999 | |
| WO | WO-2000/22430 A2 | 4/2000 | |
| WO | WO-2000/66741 A2 | 11/2000 | |
| WO | WO-2000/66791 A1 | 11/2000 | |
| WO | WO-2000/71725 A2 | 11/2000 | |
| WO | WO 01/37863 | 5/2001 | |
| WO | WO-2001/031019 A2 | 5/2001 | |
| WO | WO-2001/52885 A1 | 7/2001 | |
| WO | WO 01/64920 | 9/2001 | |
| WO | WO 01/64922 | 9/2001 | |
| WO | WO 0164922 A2 * | 9/2001 | |
| WO | WO 03/010194 | 2/2003 | |
| WO | WO 03009869 A1 * | 2/2003 | ............ A61K 39/095 |
| WO | WO 03/020756 | 3/2003 | |
| WO | WO-2003/063766 A2 | 8/2003 | |
| WO | WO 2004/032958 | 4/2004 | |
| WO | WO-2004/048404 A2 | 6/2004 | |
| WO | WO-2004/065603 A2 | 8/2004 | |
| WO | WO-2004/094596 A2 | 11/2004 | |
| WO | WO 2004/112832 * | 12/2004 | |
| WO | WO 2005/032583 A2 * | 4/2005 | |
| WO | WO 2005/102384 * | 11/2005 | |
| WO | WO-2005/106009 A2 | 11/2005 | |
| WO | WO 2006/024954 * | 3/2006 | |
| WO | WO-2006/081259 A2 | 8/2006 | |
| WO | WO 2007/000341 * | 1/2007 | |
| WO | WO 2007/060548 * | 5/2007 | |
| WO | WO-2007/127665 A2 | 11/2007 | |
| WO | WO 2008/001224 A2 * | 1/2008 | |
| WO | WO-2008/125985 A2 | 10/2008 | |
| WO | WO-2008/149238 A2 | 12/2008 | |
| WO | WO 2009/104097 * | 8/2009 | |
| WO | WO 2009/143168 A2 * | 11/2009 | |
| WO | WO-2010/028859 A1 | 3/2010 | |
| WO | WO-2010/046715 A1 | 4/2010 | |
| WO | WO-2011/110634 A1 | 9/2011 | |
| WO | WO-2011/126863 A1 | 10/2011 | |

OTHER PUBLICATIONS

Pelton et al, Expert Reviews Vaccine, 2009, 8/6:717-727.*
Broker et al, Minerva Med., 2009, 98:575-589.*
Bethell et al, Vaccine, 2002, 1/1:75-84.*
Morley et al, Vaccine, 2002, 20:666-687.*
Jacobsson et al, Scandinavian J. Infectious Diseases, 2008, 40:734-744.*
Comanducci et al, Infection and Immunity, Jul. 2004, 72/7:4217-4223.*
Bowe et al, Infection and Immunity, Jul. 2004, 72/7:4052-4060.*
Litt et al, J. Infectious Diseases, 2004, 190:1488-1497.*
Sadarangani et al, Lancet Infectious Disease, 2010, 10:112-124.*
Jodar et al, Lancet, 2002, 359:1499-1508.*
Harrison, Clinical Microbiology Reviews, Jan. 2006, 19/1:142-164.*
Tsang et al, J. Clinical Microbiology, Jun. 2007, 45/6:1753-1758.*
Cripps et al, Current Opinion in Immunology, 2002, 14:553-557.*
Lionel et al, N. Engl. J. Med., 2010, 362:1511-1520.*
Tappero et al, JAMA, Apr. 28, 1999, 281/16:1520-1527.*
Rusnick et al, Genome Biol. 2009, 10:R110.1-R110.13.*
Bentley et al, PLoS Genet., 2007, 3:230-240.*
Murphy et al, J. Infect. Dis., 2009, 200:379-389.*
Pizza et al. 2000 (Science 287: 1816-1820).*
Greenspan et al. 1999 (Defining epitopes: It's not as easy as it seems; Nature Biotechnology, 17:936-937).*
Tsang et al. 2005 (Serological Specificities of Murine Hybridoma Monoclonal Antibodies against Neisseria meningitidis Serogropu B, C, Y and W135 and Evaluation of Their Usefulness as Serogrouping Reagents by Inderct Whole-Cell Enzyme-Linked Immunosorbent Assay; Clincal and Diagnostic Laboratory Immunology 12(1):152-156).*
Guo et al. 2004 ("Protein tolerance to random amino acid change", Proceedings of the National Academy of Sciences USA, vol. 101, No. 5, pp. 9205-9210, 2004).*
Nov. 17, 1997-NM_shotgun.dbs and Dec. 15, 1997-NM.dbs, located at <ftp://ftp.sanger.ac.uk/pub/pathogens/nm/old_data/> Generated Jul. 23, 2008. 2 pages.
Adams (1996). "Should Non-Peer-Reviewed Raw DNA Sequence Data Release Be Forced on the Scientific Community?," Science, 274: 534-536.
Aderson et al. (2010). "Effectiveness of a bivalent factor H binding protein vaccine across Neisseria meningitidis serogroups," 17th International Pathogenic Neisseria Conference 2010, p. 196.
Ala'Aldeen et al. (2010) "Human antibody response to the meningococcal factor H binding protein (LP2086) during invasive disease, colonization and carriage," Vaccine 28:7667-75.
Ambrose et al. (2006). "Characterization of LP2086 expression in Neisseria meningitidis," 15th International Pathogenic Neisseria Conference 2006, p. 103.
Anderson et al. (2008). "Functional cross-reactive antibodies are elicited by a group B Neisseria meningitidis bivalent recombinant lipidated LP2086 vaccine in cynomolgusmacaques," 16th International Pathogenic Neisseria Conference (IPNC) P100, pp. 170-171.
Anderson et al. (2009). "Development of a factor H binding protein vaccine for broad protection against invasive Neisseria meningitidis serogroup B (MnB) disease," 10th European Meningococcal Disease Society Congress 2009, p. 39.

(56) References Cited

OTHER PUBLICATIONS

Anderson et al. (2009). "Epidemiology of the serogroup B Neisseria meningitidis (MnB) factor H binding protein and implications for vaccine development," European Society for Paediatric Infectious Disease Symposium 2009, p. 505.
Anderson et al. (2012). "Potential impact of the bivalent rLP2086 vaccine on Neisseria meningitidis invasive disease and carriage isolates in two adolescent populations," European Society for Paediatric Infectious Disease Symposium 2012, p. 807.
Anderson et al. (2013) "Potential impact of the bivalent rLP2086 vaccine on Neisseria meningitidis carriage and invasive serogroup B disease," Hum Vacc Immunotherap 9:471-9.
Appendix I to Statement of Grounds of Appeal filed by df-mp on Sep. 28, 2012, in relation to EP1645631, 1 page.
Appendix II to Statement of Grounds of Appeal filed by df-mp on Sep. 28, 2012, in relation to EP1645631, 2 pages.
Beernink (Jul. 2010) "Impaired immunogenicity of a meningococcal factor H-binding protein vaccine engineered to eliminate factor h binding," Clin Vac Immunol 17(7):1074-1078.
Beernink et al (Jul. 2006). "Rapid Genetic Grouping of Factor H-Binding Protein (Genome-Derived Neisserial Antigen 1870), a Promising Group B Meningococcal Vaccine Candidate," Clinical and Vaccine Immunology 13(7):758-763.
Beernink et al. (Jun. 2008). "Bactericidal antibody responses, induced by meningococcal recombinant chimeric factor H-binding protein vaccines," Infection and Immunity 76(6):2568-2575.
Beernink et al. (Sep. 2008). "Fine antigenic specificity and cooperative bactericidal activity of monoclonal antibodies directed at the meningococcal vaccine candidate factor h-binding protein," Infection and Immunity 76(9):4232-4240.
BenMohamed et al. (2002). "Lipopeptide vaccines-yesterday, today, and tomorrow," Lancet 2(7):425-431.
Bentley et al. (2004). Identification of two immunologically distinct domains on the LP2086 outer membrane lipoprotein of Neisseria meningitidis, 14th International Pathogenic Neisseria Conference 2004, p. 144.
Bernfield L. et al. (Sep. 2002). "Identification of a novel vaccine candidate for group B Neisseria meningitidis," Thirteenth International Pathogenic Neisseria Conference, Norwegian Institute of Public Health, Oslo, Norway, pp. 116 and 124.
Biswas et al. (1995). "Characterization of IbpA, the structural gene for a lactoferrin receptor in Neisseria gonorrhoeae," Infection and Immunity, 63(8): 2958-2967.
Blattner et al. (1997). "The complete genome sequence of *Escherichia coli* K-12," Science 277 (5331): 1453-1474.
Boslego et al. (1991). "Gonorrhea Vaccines," Chapter 17 In *Vaccines and Immunotherapy*, Cryz S.J. (Ed.), Pergamon Press: New York, NY, pp. 211-223.
Bouvier et al. (1991). "A gene for a new lipoprotein in the dapA-purC interval of the *Escherichia coli* chromosome," J Bacteriol 173(17):5523-5531.
Cannon (1989). "Conserved Lipoproteins of Pathogenic *Neisseria* Species Bearing the H.8 Epitope: Lipid-Modified Azurin and H.8 Outer Membrane Protein," Clinical Microbiology Reviews 2(Suppl.):S1-S4.
Cantini et al. (Mar. 2006). "Solution Structure of the Immunodominant Domain of Protective Antigen GNA 1870 of Neisseria meningitidis," *Journal of Biological Chemistry* 281(11): 7220-7227.
Capecchi et al. (2005) "*Neisseria meningitides* NadA is a new invasion which promotes bacterial adhesion to and penetration into human epithelial cells," Molecular Microbiology, 55: 687-698.
Chen, et al. (1994). "Determination of the optimal aligned spacing between the Shine-Dalgarno sequence and the translation initiation codon of *Escherichia coli* mRNAs," Nucleic Acids Res. 22(23):4953-4957.
Clinical Trial No. NCT00500032, (2007). "Blood collection for use in serological assay development from healthy adult volunteers," U.S. National Institutes of Health, retrieved online at <http://clinicaltrials.gov/ct2/show/NCT00500032?term=NCT00500032 &rank=1> 3 pages.

Clinical Trial No. NCT00808028, (2008). "A study evaluating safety and immunogenicity of meningococcal B rlp2086 vaccine in adolescents," U.S. National Institutes of Health, retrieved online at <http://clinicaltrials.gov/ct2/show/NCT00808028?term=NCT00808028 &rank=1> 4 pages.
Cohn et al. (2010). "Potential Impact of Serogroup B Vaccines: Prevalence of candidate vaccine antigens among invasive Neisseria meningitidis isolates in the United States," 17th International Pathogenic Neisseria Conference 2010, p. 77.
Cole et al. (1998). "Deciphering the biology of *Mycobacterium tuberculosis* from the complete genome sequence," Nature 394:651-653.
Cordis (2005). "Preparation of meningococcal antigens," posted online on Feb. 2, 2 pages.
Cruse et al. (2003). Illustrated Dictionary of Immunology, $2^{nd}$ Ed. CRC Press, pp. 46, 166, and 382.
Database accession No. NMB1994 (cf. XP2231040) (Tettelin et al.), uploaded Oct. 1, 2000. 337 pages.
Database UniProt (Oct. 1, 2000), "SubName: Full=Uncharacterized protein" retrieved from EBI, accession No. Q9JXV4 Database accession No. Q9JXV4. 2 pages.
Decision revoking the European Patent, filed in opposition against EP1976990, dated Nov. 11, 2013, 15 pages.
Decision to refuse a patent application, filed in the Opposition against EP1645631, dated Apr. 28, 2009, 7 pages.
Declaration by Dr. Ellen Murphy, Ph.D., dated Sep. 14, 2011, submitted in opposition proceedings for EP1645631, 4 pages.
Declaration by Dr. Julian Parkhill dated Jun. 12, 2008, submitted in opposition proceedings for EP1645631, 2 pages.
Declaration by Dr. Julian Parkhill, filed in the Opposition against EP1645631, dated Jul. 10, 2014, 5 pages.
Declaration by E. Richard Moxon dated Feb. 16, 2013, submitted in opposition proceedings for EP1645631, 5 pages.
Declaration by Ellen Murphy, filed in the Opposition against EP1645631, dated May 12, 2014, 3 pages.
Declaration by Emilio A. Emini, Ph.D., dated Nov. 2, 2011, submitted in opposition proceedings for EP1645631, 5 pages.
Declaration by Isabel Delany, dated Feb. 18, 2013, submitted in opposition proceedings for EP1645631, 5 pages.
Declaration by Prof. Paul Dunman, Ph.D., dated Sep. 25, 2012, submitted in opposition proceedings for EP1645631, 14 pages.
Declaration by Rino Rappuoli, dated Oct. 13, 2011, submitted in opposition proceedings for EP1645631, 5 pages.
Declaration by Vega Masignani dated Feb. 18, 2013, submitted in opposition proceedings for EP1645631, 4 pages.
Delgado et al. (2007). "Lipoprotein NMB0928 from Neisseria meningitidis serogroup B as a novel vaccine candidate," Vaccine 25:8420-8431.
Dinthilhac and Claverys (1997). "The adc locus, which affects competence for genetic transformation in *Streptococcus pneumoniae*, encodes an ABC transporter with a putative lipoprotein homologous to a family of streptococcal adhesins," Res Microbiol 148:119-131.
Dlawer et al. (2010). "Human antibody responses to the meningococcal factor H binding protein LP2086 during invasive disease," 17th International Pathogenic Neisseria Conference 2010, p. 130.
Donnelly et al. (2010). "Qualitative and quantitative assessment of meningococcal antigens to evaluate the potential strain coverage of protein-based vaccines," Proc Natl Acad Sci U S A, 107(45):19490-5.
Elzanowski et al. (2013). "The Genetic Codes, a compilation," Retrieved from http://www.bioinformatics.org/JaMBW/2/3/TranslationTables.html. 16 pages.
Experimental data: expression of NspA, '287' and '741' on 3 strains of bacteria, filed in opposition against EP1534326, dated Aug. 4, 2010. 2 pages.
Facts and Submissions dated May 21, 2012, in relation to EP1645631, 30 pages.
Farley J. et al. (Sep. 2002). "Characterization, cloning and expression of different subfamilies of the ORF 2086 gene from Neisseria meningitidis," Thirteenth International Pathogenic Neisseria Conference, Norwegian Institute of Public Health, Oslo, Norway, p. 124.

(56) References Cited

OTHER PUBLICATIONS

Fleischmann et al. (1995). "Whole-Genome Random Sequencing and Assembly of Haemophilus influenzae Rd," Science 269:496-501.
Fontana et al. (2002). A genomic approach Abstract from the 13th International Pathogenic Neisseria Conference, Oslo, Norway, Sep. 1-6, 2002. p. 248.
Fraser et al. (1997). "Genomic sequence of a lyme disease spirochaete, Borrelia burgdorferi," Nature 390:580-586.
Fraser et al. (1998). "Complete genome sequence of Treponema pallidum, the syphilis spirochete," Science 281:375-388.
Gene Browser, Nature Technology Corporation, filed in the Opposition against EP1645631, dated Jun. 26, 2013, 6 pages.
GenPept accession No. AAF42204, "hypothetical protein NMB1870 [Neisseria meningitidis MC58]," retrieved on Sep. 26, 2012, 2 pages.
Gervais et al. (1992). "Putative Lipoprotein Yaec Precursor," Database Swissport Acc No. p28635.
Giuliani et al. (2006). "A universal vaccine for serogroup B meningococcus," PNAS 103(29):10834-10839.
Giuliani et al. (2010). "Measuring antigen-specific bactericidal responses to a multicomponent vaccine against serogroup B meningococcus," Vaccine 28:5023-5030.
Giuliani et al. (Feb. 2005). "The Region Comprising Amino Acids 100 to 255 of Neisseria meningitidis Lipoprotein GNA 1870 Elicits Bactericidal Antibodies," Infection and Immunity 73(2): 1151-1160.
Gold and Stormo (1987). "Translation Initiation", in Escherichia con and Salmonella typhimurium, Cellular and Molecular Biology, Ed. Neidhardt, pp. 1302-1307.
Gorringe et al. (2009). "16th International Pathogenic Neisseria Conference: recent progress towards effective meningococcal disease vaccines," Human Vaccines 5(2):53-56.
Grandi (2005). "Reverse vaccinology: a critical analysis," in Encyclopedia of Genetics, Genomics, Proteomics and Bioinformatics, pp. 1322-1326.
Harris et al. (2008). "Development and qualification of serum bactericidal assays for Neisseria meningitidis serogroup B," 16th International Pathogenic Neisseria Conference 2008, p. 268-269.
Harris et al. (2010). "Robustness of the Serum Bactericidal Activity (SBA) Assay for Neisseria meningitidis serogroup B," 17th International Pathogenic Neisseria Conference 2010, p. 169.
Harris et al. (2011) "Preclinical evidence for the potential of a bivalent fHBP vaccine to prevent Neisseria meningitidis serogroup C disease," Human Vaccines 7:1 (suppl) 1-7.
Hayashi and Wu, "Identification and characterization of lipid-modified proteins in bacteria," Chapter 10 in Lipid Modifications of Proteins: A Practical Approach, Hooper and Turner (eds.), published in 1992, 27 pages.
Hem et al. (1995). "Structure and properties of aluminum-containing adjuvants," Vaccine Design. Subunit and Adjuvant Approach, pp. 249-276.
Hodge et al. (2006). "Development of a luminex-based meningococcal rLP2086-specific human IgG assay," 15th International Pathogenic Neisseria Conference 2006, p. 113.
Hoiseth et al. (2008). "LP2086 and MLST distribution in epidemiologically relevant strains of serogroup B Neisseria meningitidis," 16th International Pathogenic Neisseria Conference 2008, p. 205.
Holst et al. (2014). "Variability of genes encoding surface proteins used as vaccine antigens in meningococcal endemic and epidemic strain panels from Norway," Vaccine 32:2722-2731.
Hou et al. (2005) "Protective antibody responses elicited by a meningococcal outer membrane vesicle vaccine with overexpressed genome-derived neisserial antigen 1870," J Infect Dis 192(4):580-90.
Hung et al. (2011). "The Neisseria meningitidis macrophage infectivity potentiator protein induces cross-strain serum bactericidal sctivity and is a potential serogroup B vaccine candidate," Infect Immun 79(9):3784-3791.
Interlocutory decision in opposition proceedings, filed in the Opposition against EP1645631, dated May 21, 2012, 82 pages.

Jacobsson et al. (2009). "Prevalence and sequence variations of the genes encoding the five antigens included in the novel 5CVMB vaccine covering group B meningococcal disease" Vaccine. 27:1579-1584.
Jansen et al. (2008). "Bivalent recombinant LP2086 vaccine to provide broad protection against Neisseria meningitidis B disease: immunological correlates of protection and how to assess coverage against invasive MnB strains," 16th International Pathogenic Neisseria Conference 2008, p. 80-81.
Jansen et al. (2009). "Development of a bivalent factor H binding protein vaccine to broadly protect against invasive Neisseria meningitides serogroup B (MnB) disease," European Society for Paediatric Infectious Disease Symposium 2009, p. 311.
Jansen et al. (2010). "Estimating effectiveness for Neisseria meningitidis serogroup B (MnB) vaccine candidates composed of non-serogroup specific antigens," 17th International Pathogenic Neisseria Conference 2010, p. 37.
Jansen et al. (2011). "Monitoring the Breadth of Coverage of Meningococcal Vaccines: An Overview and Progress Update on the Pfizer Bivalent LP2086 Vaccine Program," 14th Annual Conference on Vaccine Research, 2011, p. 74.
JCVI-CMR website showing Z2491 Sanger sequence (http://cmr.jcvi.org/tigr-scripts/CMR/shared/Genomes.cgi and links). (2010) 8 pages.
Jiang et al. (2003). "Using rate of acid neutralization to characterize aluminum phosphate adjuvant," Pharma Dev Tech 8(4):349-356.
Jiang et al. (2006). "Serum IgG response induced by a bivalent recombinant LP2086 provides broad protection against serogroup B Neisseria meningitidis," 15th International Pathogenic Neisseria Conference 2006, p. 113.
Jiang et al. (2008). "Prediction of broad vaccine coverage for a bivalent rLP2086 based vaccine which elicits serum bactericidal activity against a diverse collection of serogroup B meningococci," 16th International Pathogenic Neisseria Conference 2008, p. 57-58.
Jiang et al., (2010) "Broad vaccine coverage predicted for a bivalent recombinant factor H binding protein based vaccine to prevent serogroup B meningococcal disease" Vaccine 28:6086-6093.
Johnson et al. (1999). "Analysis of the human Ig isotype response to lactoferrin binding protein a from Neisseria meningitidis," FEMS Immun. Med. Microbial. 25(4): 349-354.
Jones et al. (2009). "Generation of human serum complement lots that perform consistently for use in Neisseria meningitidis serogroup B (MnB) vaccine clinical trials," European Society for Paediatric Infectious Disease Symposium 2009, p. 566.
Juncker et al. (2003). "Prediction of lipoprotein signal peptides in gram-negative bacteria," Protein Sci 12:1652-1662.
Koeberling et al. (2007). "Improved immunogenicity of a H44/76 group B outer membrane vesicle vaccine with over-expressed genome-derived Neisserial antigen 1870," Vaccine 25(10):1912-1920.
Koeberling et al. (2008). "Bactericidal antibody responses elicited by a meningococcal outer membrane vesicle vaccine with overexpressed factor H-binding protein and genetically attenuated endotoxin," J. Infect. Dis., 198(2):262-270.
Koeberling et al. (2009). "Meningococcal outer membrane vesicle vaccines derived from mutant strains engineered to express factor H binding proteins from antigenic variant groups 1 and 2," Clin Vac Immunol, 16(2):156-162.
Kovacs-Simon et al. (2011). "Lipoproteins of Bacterial Pathogens," Infect Immun 79(2):548-561.
Legrain et al. (1995). "Production of Lipidated Meningococcal Transferrin Binding Protein 2 in Escherichia Coli," Protein Expression and Purification 6:570-578.
Lewis et al. (2010). "The meningococcal vaccine candidate neisserial surface protein A (NspA) binds to factor H and enhances meningococcal resistance to complement," PLoS Pathogens 6(7):e1001027.
Liebl et al. (1997). "Properties and gene structure of the Thermotoga maritima alpha-amylase AmyA, a putative lipoprotein of a hyperthermophilic bacterium," J Bacteriol 179(3):941-948.

(56) References Cited

OTHER PUBLICATIONS

Liechti et al. (2012). "Outer membrane biogenesis in *Escherichia coli*, Neisseria meningitidis, and Helicobacter pylori: paradigm deviations in H. pylori," Front Cell and Infect Microbiol 2:article 29. 18 pages.
Lindblad, (2004). "Aluminium compounds for use in vaccines," Immunol Cell Biol.,82(5):497-505.
Lucidarme et al., 2010 "Characterization of fHbp, nhba (gna2132), nadA, porA, and sequence type in group B meningococcal case isolates collected in England and Wales during Jan. 2008 and potential coverage of an investigational group B meningococcal vaccine" Clinical and Vaccine Immunology 17(6):919-929.
Madico et al. (2006). "The meningococcal vaccine candidate GNA1870 binds the complement regulatory protein factor H and enhances serum resistance," J Immunol 177(1):501-510.
Marshall et al. (2008). "A randomized, placebo-controlled, double-blind, phase 1 trial of ascending doses of meningococcal group B rLP2086 vaccine in healthy adults," 16th International Pathogenic Neisseria Conference 2008, p. 271-272.
Marshall et al. (2011). "Phase I randomised controlled clinical trial of safety and immunogenicity of a meningococcal B bivalent LP2086 vaccine in healthy toddlers," European Society for Paediatric Infectious Disease Symposium 2011, p. 189.
Marshall et al. (2012) "Safety and immunogenicity of a meningococcal B bivalent rLP2086 vaccine in healthy toddlers aged 18-36 months: A phase 1 randomized-controlled clinical trial," Ped Infect Dis J 31:1061-8.
Marshall et al. (2013) "A phase 2 open-label safety and immunogenicity study of a meningococcal B bivalent rLP2086 vaccine in healthy adults," Vaccine 31:1569-75.
Martin et al. (1998). "New Zealand epidemic of meningococcal disease identified by a strain with phenotype B:4:P1.4," JID 177:497-500.
Martin et al. (2003). "Experimentally revised repertoire of putative contingency loci in *Neisseria meningitidis* strain MC58: evidence for a novel mechanism of phase variation," Molecular Microbiology 50(1):245-257.
Mascioni et al. (2008). "Determination of the domain and solution structure of rLP2086, a meningococcal vaccine candidate and human factor H binding protein," 16th International Pathogenic Neisseria Conference 2008, p. 77-78.
Mascioni et al. (2009) "Structural basis for the immunogenic properties of the meningococcal vaccine candidate LP2086," J Biol Chem 284:8738-46.
Mascioni et al. (2010) "NMR dynamics and antibody recognition of the meningococcal lipidated outer membrane protein LP2086 in micellar solution," Biochim Biophys Acta 1798:87-93.
Masignani V. (Mar. 17, 2003). "Vaccination against Neisseria meningitidis using three variants of the lipoprotein GNA1870," J. Exp. Med. 197(6):789-799.
McNeil et al. (2009) "Detection of LP2086 on the cell surface of Neisseria meningitidis and its accessibility in the presence of serogroup B capsular polysaccharide," Vaccine 27:3417-21.
McNeil et al. (2010). "Anti-fHBP antibodies elicited after immunization with a recombinant fHBP vaccine candidate (rLP2086) can displace human Factor H from the surface of Serogroup B Meningococci," 17th International Pathogenic Neisseria Conference 2010, p. 94.
McNeil et al. (2013) "Role of factor H binding protein in Neisseria meningitidis virulence and its potential as a vaccine candidate to broadly protect against meningococcal disease," Microbiol Mol Biol Rev 77:234.
Meyer et al. (1984). "Pilus genes of *Neisseria gonorrheae*: Chromosomal organization and DNA sequence," Proc. Natl. Acad. Sci. USA 81: 6110-6114.
Milagres et al. (1998). "Specificity of bactericidal antibody response to serogroup B meningococcal strains in Brazilian children after immunization with an outer membrane vaccine," Infection and Immun. 66(10): 4755-4781.
Minutes of the oral proceedings, filed in the Opposition against EP1645631, dated Feb. 11, 2014, 4 pages.
Munkley, et al. (1991). "Blocking of bactericidal killing of Neisseria meningitidis by antibodies directed against slacc 4 outer membrane proteins," Microbial Pathogenesis 11: 447-452.
Murphy et al. (2008). "Sequence diversity of vaccine candidate LP2086 in Neisseria meningitidis serogroup B strains causing invasive disease," 16th International Pathogenic Neisseria Conference 2008, p. 61.
Murphy et al. (2010). "Prevalence of Factor H Binding Protein (fHBP) Variants in *N. meningitidis* Carriage Isolates," 17th International Pathogenic Neisseria Conference 2010, p. 96.
Nassif (2000). "A Furtive Pathogen Revealed," Science 287:1767-1768.
Notice of Opposition against EP 1562983, filed on Jul. 1, 2014, 25 pages.
Notice of Opposition against EP1645631, filed in the Opposition against EP1645631, dated Jul. 23, 2008, 25 pages.
Notice of Opposition filed May 24, 2012, filed in opposition against EP1976990, 19 pages.
Novartis (Jan. 22, 2013) "Novartis receives EU approval for Bexsero®, first vaccine to prevent the leading cause of life-threatening meningitis across Europe," Media Release, 3 pages.
Novartis (Jun. 9, 2011). "Novartis candidate vaccine Bexsero® shows significant potential in providing broad coverage against meningococcal serogroup B infections." Media Release, 6 pages.
Novartis (Oct. 9, 2008) "New Phase II data show Novartis investigational Meningitis B vaccine may also protect infants six months and older," Media Release, 4 pages.
Opponent's Further Submission in Preparation of the Oral Proceedings, filed in the Opposition against EP1645631, dated Nov. 3, 2011, 6 pages.
Opponent's Response to the Patentee's Submission dated Feb. 18, 2013, filed in the Opposition against EP1645631, dated Jul. 24, 2014, 34 pages.
Opponents Final Written Submission in Preparation of Oral Proceedings, filed in the Opposition against EP1645631, dated Sep. 14, 2011, 28 pages.
ORF Finder (2013). "Bacterial Code," Retrieved from http://www.ncbi.nlm.nih.gov/gorf/gorf.html, 3 pages.
Pajon et al. (2010). "Frequency of factor H-binding protein modular groups and susceptibility to cross-reactive bactericidal activity in invasive meningococcal isolates" Vaccine 28:2122-2129.
Pajon et al. (2012). "Design of meningococcal factor H binding protein mutant vaccines that do not bind human complement factor H," Infect Immun 80:2667-2677.
Parkhill et al. (2000). "Complete DNA Sequence of a Serogroup A Strain of Neisseria meningitides Z2491," Nature, 404(6777):502-506.
Parkhill, "Campylobacter jejuni genome sequence at the Sanger Centre," Post on BIOSCI/Bionet of May 8, 1998. 1 page.
Patentee's Submissions under Rule 116 EPC, filed in the Opposition against EP1645631, dated Sep. 13, 2011, 13 pages.
Patentees' Response to Opposition against European Patent EP1645631, granted on Oct. 24, 2007, 13 pages.
Pettersson, et al. (2006). "Vaccine potential of the Neisseria meningitidis lactoferrin-binding proteins LbpA and LbpB," Vaccine 24(17):3545-3557.
Pillai et al. (2005) "Outer membrane protein (OMP) based vaccine for Neisseria meningitidis serogroup B," Vaccine 23(17-18):2206-2209.
Pizza et al. (2008) "Factor H-binding protein, a unique meningococcal vaccine antigen" Vaccine 26S:I46-8.
Plikaytis et al. (2012). "Interlaboratory standardization of the sandwich enzyme-linked immunosorbent assay designed for MATS, a rapid, reproducible method for estimating the strain coverage of investigational vaccines," Clin Vaccine Immunol, (10):1609-17.
Progress through the Sanger Institute FTP server (May 12, 2009), 15 pages.
Prosite, "ScanProsite Results Viewer: USERSEQ1 (280aa)," retrieved on Jun. 21, 2012, 1 page.
PSORT analysis of 200 of the sequences disclosed in PCT/US99/09346 (Jan. 1, 2010), 209 pages.

(56) References Cited

OTHER PUBLICATIONS

PSORT analysis of Seq ID Nos. 4 and 6, and of 'Contig295' 300mer (May 8, 2009), 5 pages.
PSORT prediction result for SEQ ID No. 2 (Mar. 30, 2010), 1 page.
Pugsley (1993). "The complete general secretory pathway in gram-negative bacteria," Microbiological Rev 5(1):50-108.
Renauld-Mongenie et al. (1997). "Identification of Human Transferrin-Binding Sites Within Meningococcal Transferrin-Binding Protein B," *J. Bacteriology* 197(20):6400-6407.
Response to Appeal filed by Carpmaels & Ransford dated Feb. 18, 2013, in relation to EP1645631, 21 pages.
Response to Appeal filed by df-mp dated Feb. 18, 2013, in relation to EP1645631, 28 pages.
Response to Communication, filed in EP Application No. 07075161.5. dated Oct. 28, 2009. 2 pages.
Richmond et al. (2008). "A randomized, observer-blinded, active control, phase 1 trial of meningococcal serogroup B rLP2086 vaccine in healthy children and adolescents aged 8 to 14 years," 16th International Pathogenic Neisseria Conference 2008, p. 270-271.
Richmond et al. (2010). "Safety & immunogenicity of serogroup B Neisseria meningitidis (MnB) rLP2086 vaccine in adults and adolescent subjects: overview of 3 clinical trials," 17th International Pathogenic Neisseria Conference 2010, p. 37.
Richmond et al. (2011). "Phase II randomised controlled trial of safety and immunogenicity of a meningococcal B bivalent vaccine (rLP2086) in healthy adolescents," European Society for Paediatric Infectious Disease Symposium 2011, p. 192.
Richmond et al. (2012) "A bivalent Neisseria meningitidis recombinant lipidated factor H binding protein vaccine in young adults: Results of a randomized, controlled, dose-escalation phase 1 trial," Vaccine 30(43):6163-74.
Richmond et al. (2012) "Safety, immunogenicity, and tolerability of meningococcal serogroup B bivalent recombinant lipoprotein 2086 vaccine in healthy adolescents: a randomized, single-blind, placebo-controlled, phase 2 trial," Lancet Infect Dis 12:597-607.
Rinaudo et al. (2009). "Vaccinology in the genome era", The Journal of Clinical Investigation, 119(9):2515-2525.
Sandbu et al. (2007). "Immunogenicity and safety of a combination of two serogroup B meningococcal outer membrane vesicle vaccines," Clin Vaccine Immunol, 14(9):1062-9.
Sanger Centre's "Projects" website as of Dec. 10, 1997 as retrievable via http://web.archive.org. 1 page.
Scarselli et al. (Feb. 13, 2009). "Epitope Mapping of a Bactericidal Monoclonal Antibody against the Factor H Binding Protein of Neisseria meningitides," Journal of Molecular Biology 386(1):97-108.
Schneider et al. (Apr. 16, 2009) "Neisseria meningitidis recruits factor H using protein mimicry of host carbohydrates," Nature 458(7240):890-893.
Seeber et al. (1991). "Predicting the adsorption of proteins by aluminum-containing adjuvants," Vaccine 9(3):201-203.
Seib et al. (2011). "Characterization of Diverse Subvariants of the Meningococcal Factor H (fH) Binding Protein for Their Ability to Bind fH, to Mediate Serum Resistance, and to Induce Bactericidal Antibodies," Infect Immun, 79(2):970-81.
Sequence for "Putative Lipoprotein [*Neisseria Meningitidis* Z2491]," NCBI Reference Sequence: YP_002342062.1, Mar. 30, 2000. 2 pages.
Serruto et al. (2009). "Genome-based approaches to develop vaccines against bacterial pathogens," Vaccine 27:3245-3250.
Serruto et al. (2010). "Neisseria meningitidis GNA2132, a heparin-binding protein that induces protective immunity in humans," PNAS 107(8):3770-3775.
Sheldon et al. (2011). "Phase 1, Randomized, Open-Label, Study to Assess the Safety and Immunogenicity of Serogroup B Neisseria Meningitidis (Mnb) rLP2086 Vaccine in Healthy Adults," 14th Annual Conference on Vaccine Research, 2011, p. 59-60.
Sheldon et al. (2012) "A phase 1, randomized, open-label, active-controlled trial to assess the safety of a meningococcal serogroup B bivalent rLP2086 vaccine in healthy adults," Hum Vacc Immunotherap 8:1-8.
Shevchik et al. (1996). "Characterization of pectin methylesterase B, an outer membrane lipoprotein of Erwinia chrysanthemi 3937," Mole Microbiol 19(3):455-466.
Sprengart et al. (1997). "Functional importance of RNA interactions in selection of translation initiation codons," Molecular Microbiology, 24(1): 19-28.
Statement of Grounds of Appeal filed by Carpmaels & Ransford dated Oct. 4, 2012, in relation to EP1645631, 9 pages.
Statement of Grounds of Appeal filed by df-mp dated Sep. 28, 2012, in relation to EP1645631, 54 pages.
Submission of the Patentee dated Jul. 6, 2012, filed Jun. 24, 2014, in the Opposition against EP1645631, 4 pages.
Summons to oral proceedings pursuant to Rule 115(1) EPC, filed in the Opposition against EP1645631, dated Nov. 11, 2013, 12 pages.
Supplemental Submissions in Opposition against European Patent EP1645631, dated Oct. 24, 2007. Opposition filed on May 25, 2010. 28 pages.
Supplementary Declaration by Dr. Julian Parkhill, dated May 10, 2010, submitted in opposition proceedings for EP1645631, 4 pages.
Supplementary declaration by Ellen Murphy dated Sep. 26, 2012, submitted in opposition proceedings for EP1645631, 3 pages.
Supplementary declaration by Prof. Paul Dunman, Ph.D., dated Sep. 25, 2012, submitted in opposition proceedings for EP1645631, 14 pages.
Supplementary Submission to the Grounds of Appeal, filed in the Opposition against EP1645631, dated Sep. 28, 2012, 2 pages.
Sutcliffe and Russell (1995). "Lipoproteins of gram-positive bacteria," J Bacteriol 177(5):1123-1128.
Swaminathan (1996). "Molecular cloning of the three base restriction endonuclease R.CviJI from eukaryotic Chlorella virus IL-3A," Nucleic Acids Research, 24(13): 2463-2469.
Tavano et al. (2011). "Mapping of the Neisseria meningitidis NadA cell-binding site: Relevance of predicted α-helices in the NH2-terminal and dimeric coiled-coil regions," J Bacteriol 193(1):107-115.
Telford et al. (2003). "Genomic and Proteomics in Vaccine Design", in *New Bacterial Vaccines*, edited by Ellis et al. Kleweur Academic/Plenum Publishers, USA. pp. 1-11.
Tettelin et al. (Mar. 10, 2000). "Complete Genome Sequence of Neisseria meningitidis Serogroup B Strain MC58," Science 287(5459):1809-1815.
The printed output from the NCBI open reading frame finder (Oct. 20, 2008), 12 pages.
TIGR Microbial Database, filed in the Opposition against EP1645631, dated Jun. 20, 2012, 14 pages.
TIGR website as of 1998, 8 pages.
Tramont, (1976) "Specificity of inhibition of epithelial cell adhesion of Neisseria gonorrhoeae." Infection and Immunity 14:593-595.
Turner et al. (2006). "Characterization of MspA, an Immunogenic Autotransporter Protein That Mediates Adhesion of Epithelial and Endothelial Cells in *Neisseria meningitidis*," Infection and Immunity 74(5):2957-2964.
United States Office Action dated Feb. 11, 2009, for U.S. Appl. No. 10/181,600, filed Jan. 17, 2001, 5 pages.
United States Office Action dated Jul. 24, 2008, for U.S. Appl. No. 10/181,600, filed Jan. 17, 2001, 23 pages.
United States Office Action dated Jul. 7, 2009, for U.S. Appl. No. 10/181,600, filed Jan. 17, 2001, 23 pages.
U.S. Appl. No. 60/098,685, "*Neisseria* Spp, Polypeptide, Gene Sequence and Uses Thereof," filed Sep. 1, 1998. 82 pages.
U.S. Appl. No. 60/647,911, "GNA 1870-based vesicle vaccines for broad spectrum protection against diseases caused by Neisseria meningitidis," filed Jan. 27, 2005. 99 pages.
Van der Lay et al. (1995). "Construction of Neisseria Meningitidis Strains Carrying Multiple Chromosomal Copies of the PorA Gene for Use in Production of a Multivalent Outer Membrane Vesicle Vaccine," *Vaccine* 13(4): 401-407.

(56) References Cited

OTHER PUBLICATIONS

Vermont et al. (2003). "Cross-reactivity of antibodies against PorA after vaccination with a meningococcal B outer membrane vesicle vaccine," Infect Immun 71(4):1650-1655.
Vesikari et al. (2013). "Immunogenicity and safety of an investigational multicomponent, recombinant, meningococcal serogroup B vaccine (4CMenB) administered concomitantly with routine infant and child vaccinations: results of two randomized trials," Lancet 381:625-35.
von Heijne (1989). "The structure of signal peptides from bacterial lipoproteins," Protein Engineering 2(7):531-534.
Voulhoux and Tommassen (2002). "Transport of lipoproteins to the cell surface in Neisseria meningitidis," 13th International Pathogenic Neisseria Conference 2002, p. 31.
Wang et al. (2010). "Prevalence and genetic diversity of candidate vaccine antigens among invasive Neisseria meningitidis isolates in the United States," 17th International Pathogenic Neisseria Conference 2010, p. 122.
Welsch et al. (2002). "Genome-derived antigen (GNA) 2132 elicits protective serum antibodies to groups B and C Neisseria meningitidis strains," 13th International Pathogenic Neisseria Conference 2002, p. 25.
Welsch et al. (2003). "Antibody to genome-derived neisserial antigen 2132, a Neisseria meningitidis candidate vaccine, confers protection against bacteremia in the absence of complement-mediated bactericidal activity" Journal of Infectious Diseases 188(11):1730-1740.
Welsch et al. (2004). "Protective Activity of Monclonal Antibodies to Genome-Derived Neisserial Antigen 1870, a Neisseria meningitidis Candidate Vaccine," *The Journal of Immunology* 172: 5606-5615.
Welsch et al. (2007) "A novel mechanism for complement-mediated killing of encapsulated Neisseria meningitidis elicited by monoclonal antibodies to factor H-binding protein (genome-derived Neisserial antigen 1870)" Molecular Immunology 44(1-3):256.
Welsch et al. (Apr. 1, 2008). "Complement-dependent synergistic bactericidal activity of antibodies against factor H-binding protein, a sparsely distributed meningococcal vaccine antigen," J Infect Dis 197(7):1053-1061.
Woods, et al. (1987). "Resistance to meningococcemia apparently conferred by anti-H.8 monoclonal antibody is due to contaminating endotoxin and not to specific immunoprotection," Infection and Immunity 55(8):1927-1928.
Written Submission to Oral Proceedings, filed in opposition against EP1976990, dated Jul. 24, 2013, 11 pages.
Wu et al. (1996). "A protein class database organized with ProSite protein groups and PIR superfamilies," J Comp Biol 3(4):547-561.
York et al. (2010). "fHBP epidemiology of invasive meningococcal B isolates from Spain and Germany: age based," 17th International Pathogenic Neisseria Conference 2010, p. 109.
Zhu et al. (2004). "Evaluation of the purified recombinant lipidated P2086 protein as a vaccine candidate for group B Neisseria meningitidis in a murine nasal challenge model," 14th International Pathogenic Neisseria Conference 2004, p. 199.
Zhu et al. (2005) "Evaluation of recombinant lipidated P2086 protein as a vaccine candidate for group B Neisseria meningitidis in a murine nasal challenge model," Infect Immun 73(10):6838-45.
Zhu et al. (2006) "Intranasal immunization of mice with recombinant lipidated P2086 protein reduces nasal colonization of group B Neisseria meningitidis," Vaccine 24:5420-5.
Zhu et al. (2006). "Effective immunization strategy against group B Neisseria meningitidis using purified recombinant lipidated P2086 protein," 15th International Pathogenic Neisseria Conference 2006, p. 47.
Zlotnick et al. (2009). "Epidemiology of the serogroup B Neisseria meningitidis (MnB) factor H binding protein in strains sampled from Spain and Germany in the years 2001-2006," 10th European Meningococcal Disease Society Congress 2009, p. 81.
Zlotnick et al. (2010). "Biochemical and biophysical analysis indicates conformation plays an important role in the binding of hfH and antibodies to the fHBP of N. meningitidis," 17th International Pathogenic Neisseria Conference 2010, p. 38.
Zollinger et al. (2010). "Design and evaluation in mice of a broadly protective meningococcal group B native outer membrane vesicle vaccine," Vaccine, 28(31):5057-5067.
Alignment of Seq ID No. 19 of EP2327719 against Seq ID Nos. 92, 94, 96, 98, 100, 102, 104, 106, and 108 of WO/2003/063766, filed in opposition against EP2327719, submitted May 20, 2015, 9 pages.
Alignment of Seq ID No. 42 of EP2258716 against Seq ID No. 41 of EP2258716, filed in opposition against EP2258716, submitted Apr. 16, 2015, 1 page.
Alignment of Seq ID No. 42 of EP2258716 against Seq ID Nos. 50, 52, 54, 56, 58, 60, 62, 64, 66, 68, 70, and 72 of WO/2003/063766, filed in opposition against EP2258716, submitted Apr. 16, 2015, 12 pages.
Beernink et al. (2011). "A meningococcal factor H binding protein mutant that eliminates factor H binding enhances protective antibody responses to vaccination," J Immunol, 186(6):3606-14.
Brendish and Read. (2015). "Neisseria meningitidis serogroup B bivalent factor H binding protein vaccine," Expert Rev. Vaccines, 14(4):493-503.
Experimental Report, Submitted on Mar. 23, 2015, filed in relation to EP2411048, 2 pages.
Magagnoli et al. (2009). "Structural organization of NadADelta(351-405), a recombinant MenB vaccine component, by its physicochemical characterization at drug substance level," Vaccine, 27(15):2156-70.
Notice of Opposition, filed in Opposition against EP1737486, dated Nov. 27, 2013, 28 pages.
Notice of opposition, filed in opposition against EP2258716, dated Apr. 16, 2015, 12 pages.
Notice of opposition, filed in opposition against EP2327719, dated May 20, 2015, 14 pages.
Novartis internal data, filed in relation to EP1902726, submitted on Apr. 13, 2015, 1 page.
Patentee's response to notice of opposition, filed in opposition against EP1562983, dated Feb. 16, 2015, 9 pages.
Post-filing Data, submitted by patentee on Jul. 6, 2012, filed in opposition against EP1737486, 2 pages.
Response to Notice of Opposition, filed in opposition against EP1737486, dated Jun. 26, 2014, 9 pages.
Rosenstein et al. (2001). "Meningococcal disease," N Engl J Med, 344(18):1378-88.
Statement of Grounds of Appeal, dated Mar. 23, 2015, filed in relation to EP2411048, 8 pages.
Statement of grounds of appeal, filed in relation to EP1902726, dated Apr. 13, 2015, 9 pages.
Submission in opposition proceedings by Carpmaels and Ransford filed in EP1737486 on Jun. 12, 2015, 2 pages.
Submission in opposition proceedings by Pfizer Inc. filed against EP1737486 on Jun. 12, 2015, 7 pages.
UniProt accession No. C0JF81, Murphy et al., Last modified on May 5, 2009. 4 pages.
U.S. Appl. No. 60/328,101, "Novel immunogenic compositions for the prevention and treatment of meningococcal disease," filed Oct. 11, 2001. 253 pages.
U.S. Appl. No. 60/406,934, "Novel immunogenic compositions for the prevention and treatment of meningococcal disease," filed Aug. 30, 2002. 190 pages.
Aebi et al. (1997). "A protective epitope of Moraxella catarrhalis is encoded by two different genes," Infect Immun. 65(11):4367-77.
Amended Defence and Counterclaim, Jul. 24, 2015, Claim No. HP-2015-000022, Glaxosmithkline *UK LTD* v. *Wyeth Holdings LLC,* 4 pages.
Annex 1 to the Amended Defence and Counterclaim, Jun. 24, 2015, Claim No. HP-2015-000022, Glaxosmithkline *UK LTD* v. *Wyeth Holdings LLC,* 40 pages.
Bernfield et al. (2002). "Identification of a novel vaccine candidate for group B Neisseria meningitidis," 13th International Pathogenic Neisseria Conference 2002, Poster, 20 pages.
CECMED (Dec. 2, 2011), "Resumen de las Caracteristicas del Producto: VA-MENGOC-BC," Ministerio de Salud Publica de Cuba, 4 pages. (3 page English translation included).

(56) References Cited

OTHER PUBLICATIONS

Claimants Amended Grounds of Invalidity under CPR 17.1 (2)(a) on Jul. 16, 2015, in respect of European Patent (UK) No. 2,343,308. In the High Court of Justice Chancery Division Patents Court, between GlaxoSmithKline UK Limited and Wyeth Holdings LLC. 9 pages.
Database UniProt (Feb. 6, 2007). Submitted name: Putative lipoprotein, Uniprot accession No. A1IQ30, PIR No. G81977, retrieved Jan. 20, 2016 from <http://www.uniprot.org/uniprot/A1IQ30>, 7 pages.
de Moraes JC, et al. (1992). Protective efficacy of a serogroup B meningococcal vaccine in Sao Paulo, Brazil. Lancet 340: 1074-1078.
Debbag et al. (1994). "Evaluacion de las reacciones adversas asociadas con la vacuna antimeningococcica BC. Informe perliminar sobre 8,117 vacunados." Rev Hosp Ninos BAires, No. 158/159, 6 pages. (6 page English translation included).
Decision of Technical Board of Appeal for EP942983, dated Nov. 14, 2013, filed in relation to EP1645631, 28 pages.
Decision revoking EP1737486, filed in opposition against EP1737486, dated Oct. 28, 2015, 28 pages.
Farley et al. (2002). "Characterization, cloning and expression of different subfamilies of the ORF 2086 gene from Neisseria meningitidis," 13th International Pathogenic Neisseria Conference 2002, Poster, 15 pages.
Fukasawa, Lucila O. et al, (2003) "Immune response to native NadA from Neisseria meningitidis and its expression in clinical isolated in Brazil." Journal of Medical Microbiology, vol. 52, pp. 121-125.
Further submissions by patentee, dated Feb. 3, 2016, filed in relation to EP1645631 appeal, 9 pages.
Galeano et al. (1995). "Efectividad de una vacuna antimeningococcica en una cohorte de itagui, Colombia, 1995," Epidemiologico de Antioquia 20(2), 8 pages. (9 page English translation included).
Gil et al. (2009). "Proteomic study via a non-gel based approach of meningococcal outer membrane vesicle vaccine obtained from strain CU385," Human Vaccines 5(5):347-356.
Notice of opposition against EP2343308, filed in opposition against EP1562983, submitted Jan. 11, 2016, 21 pages.
Ochoa, Rolando (2008). "Main projects on research, development and manufacturing of human vaccines," excerpt from presentation at BioQatar Symposium 2008, 4 slides.
Perez et al. (2010). "Community acquired bacterial meningitis in Cuba: a follow up of a decade," BMC Infectious Diseases 10:130, 9 pages.
Pfizer observations, filed in opposition against EP1562983, dated Apr. 27, 2012, 7 pages.
Pfizer observations, filed in opposition against EP1562983, dated May 12, 2011, 7 pages.
Response by opponent, filed in opposition against EP1562983, dated Jan. 11, 2016, 12 pages.
Response to Notice of Opposition by Novartis Vaccines and Diagnostics SRL for EP2327719, dated Jan. 6, 2016. 10 pages.
Response to Notice of Opposition, filed in opposition against EP2258716, dated Dec. 3, 2015, 8 pages.
Richmond et al. (Sep. 7-12, 2008). "A randomized, observer-blinded, active control, phase 1 trial of meningococcal serogroup B rLP2086 vaccine in healthy children and adolescents aged 8 to 14 years." 16th International Pathogenic Conference; Rotterdam, the Netherlands. P212. 2 pages.
Rodriguez et al. (1999). "The epidemiological impact of antimeningococcal B vaccination in Cuba," Mem Inst Oswaldo Cruz 94(4):433-440.
Sierra GV, et al. (1991). Vaccine against group B Neisseria meningitidis: protection trial and mass vaccination results in Cuba. NIPH Ann 14: 195-207.
Statement of grounds of appeal, dated Mar. 7, 2016, filed in relation to EP1737486, 9 pages.
Statement of Grounds of Appeal, filed in relation to EP2353608, dated Jul. 22, 2015, 8 pages.
Summons to Attend Oral Hearings dated May 3, 2016, for EP2275129, 8 pages.
Sworn Statement in EP1645631 from Isabel Delany, signed Feb. 1, 2016. 2 pages.
Tavano et al. (Jul. 2000). "The membrane expression of Neisseria meningitidis adhesin A (NadA) increases the proimmune effects of MenB OMVs on human macrophages, compared with NadA-OMVs, without further stimulating their proinflammatory activity on circulating monocytes," J Leukoc Biol 86(1):143-153.
U.S. Appl. No. 61/358,816, "Combinations of Meningococcal Factor H Binding Proteins," filed Jun. 25, 2010. 48 pages.
Written Submissions from the Patentee, GlaxoSmithKline Biologicals SA for EP1645631, dated Feb. 3, 2016, 10 pages.
Comanducci et al., "*NadA, a Novel Vaccine Candidate of Neisseria meningitids*" 2002 J. Exp. Med. 197:789-799.
Pizza et al., "*Identification of Vaccine Candidates Against Serogroup B Meningococcus by Whole-Genome Sequencing*" 2000 Science 287: 1816-1820.
The sequence published as GenBank GI:7227353 (AAF42408.1) entitled "hemolysin, putative [Neisseria meningitidis]" dated Mar. 10, 2000; 2 total pages; available at https://www.ncbi.nlm.nih.gov/protein/7227353?sat=8&satkey=664384.
The sequence published as GenBank AAF41995.1 entitled "hemolysin, putative [Neisseria meningitidis]" dated Mar. 10, 2000; 2 total pages; available at https://www.ncbi.nlm.nih.gov/protein/7226897?sat=8&satkey=664341.
Sanchez, S. et al. "In vitro induction of memory-driven responses against Neisseria meningitidis by priming with Neisseria lactamica," Vaccine, 20 (23-24): 2957-2963 (2002).
Fletcher, L. et al. "Vaccines Potential of the Neisseria meningitidis 2086 Lipoprotein," Infection and Immunity, 72 (4): 2088-2100 (2004).
Menendez, T. et al. "Immunisation with phage-displayed variable region 2 from meningococcal PorA outer membrane protein induces . . ." Immunology Letters, 78 (3): 143-148 (2001).

\* cited by examiner

IMMUNISING AGAINST MENINGOCOCCAL SEROGROUP Y USING PROTEINS

RELATED APPLICATIONS

This application is the U.S. National Phase of International Application No. PCT/IB2005/001279, filed Apr. 22, 2005 and published in English, which claims priority to Great Britain Application No. 0408977.7, filed Apr. 22, 2004. The teachings of the above applications are incorporated herein in their entirety by reference.

TECHNICAL FIELD

This invention is in the fields of immunology and vaccinology. In particular, it relates to antigens from *Neisseria meningitidis* (meningococcus) and their use in immunisation.

BACKGROUND ART

*N. meningitidis* is a non-motile, Gram-negative human pathogen that colonises the pharynx and causes meningitis (and, occasionally, septicaemia in the absence of meningitis). It causes both endemic and epidemic disease. Following the introduction of the conjugate vaccine against *Haemophilus influenzae*, *N. meningitidis* is the major cause of bacterial meningitis in the USA.

Based on the organism's capsular polysaccharide, various serogroups of *N. meningitidis* have been identified. Serogroup A is the pathogen most often implicated in epidemic disease in sub-Saharan Africa. Serogroups B and C are responsible for the vast majority of cases in the USA and in most developed, countries. Serogroups W135 and Y are responsible for the rest of the cases in the USA and developed countries. After serogroup, classification includes serotype, serosubtype and then immunotype, and the standard nomenclature lists serogroup, serotype, serosubtype, and immunotype, each separated by a colon e.g. B:4:P1.15:L3, 7,9. Within serogroup B, some lineages cause disease often (hyperinvasive), some lineages cause more severe forms of disease than others (hypervirulent), and others rarely cause disease at all. Seven hypervirulent lineages are recognised, namely subgroups I, III and IV-1, ET-5 complex, ET-37 complex, A4 cluster and lineage 3. These have been defined by multilocus enzyme electrophoresis (MLEE), but multilocus sequence typing (MLST) has also been used to classify meningococci [ref. 1].

To date, vaccines against serogroup A, C, W135 and Y have used their capsular saccharides as antigens. A licensed human polysaccharide vaccine against these four serogroups has been known for many years [2,3]. More recently the focus has remained on saccharides, but the conjugation to carrier proteins. Conjugate vaccines against serogroup C have been approved for human use, and include MENJUGATE™ [4], MENINGITEC™ and NEISVACC™. Mixtures of conjugates from serogroups A+C are known [5,6] and from serogroups A+C+W135+Y have been reported [7-10].

The capsular saccharide of serogroup B cannot be used for vaccination because it is a self-antigen in humans. Chemically-modified serogroup B saccharides have been proposed [11] but have not been adopted for clinical use. Vaccines based on outer-membrane vesicles have also been tested [e.g. see ref. 34], but the protection afforded by these vaccines is typically restricted to the strain used to make the vaccine. Genome sequences for serogroups A [12] and B [13,14] have been reported, and the serogroup B sequence has been studied to identify vaccine antigens [e.g. refs. 15 to 20]. Candidate antigens have been manipulated to improve heterologous expression [refs. 21 to 23].

The established dogma for meningococcus is thus that immunisation against serogroups A, C, W135 and Y shall be based on the four different capsular saccharides, and that immunisation against serogroup B shall not be based on the capsular saccharide.

DISCLOSURE OF THE INVENTION

In contrast to this dogma, the inventors have found that immunisation against serogroups A, C, W135 and Y (and against serogroup Y in particular) can be achieved using polypeptide antigens. Moreover, they have found that serogroup B polypeptides can achieve this protection, thus permitting a single polypeptide-based vaccine to be used for protecting against all of serogroups A, B, C, W135 and Y.

Thus the invention provides a method of immunising a subject against infection by serogroup Y of *Neisseria meningitidis*, comprising administering to the subject a composition comprising one or more immunogenic polypeptides. Similarly, the invention provides the use of one or more immunogenic polypeptides in the manufacture of a medicament for immunising a subject against infection by serogroup Y of *N. meningitidis*.

The invention also provides a method of immunising a subject against infection by, serogroup Y of *Neisseria meningitidis*, comprising administering to the subject a composition comprising meningococcal OMVs; Similarly, the invention provides the use of meningococcal OMVs in the manufacture of a medicament for immunising a subject against infection by serogroup Y of *N. meningitidis*.

The methods and uses are preferably for immunising a subject against infection by serogroup Y and also against at least one of serogroups A, B, C and W135. Where a subject is being immunised against a given serogroup of meningococcus then the composition preferably does not include a capsular saccharide from that serogroup (either conjugated or non-conjugated). Thus preferred compositions do not include a capsular saccharide from serogroup Y, and may also not include a capsular saccharide from serogroups A, B, C and/or W135.

Compositions for use according to the invention can be prepared using known techniques, such as the techniques for preparing meningococcal polypeptide antigens disclosed in references 15-24, or the . known techniques for preparing OMVs disclosed in references 34-38. The use of purified polypeptide antigens is preferred to the use of outer membrane vesicles.

Vaccines against pathogens such as hepatitis B virus, diphtheria and tetanus typically contain a single protein antigen (e.g. the HBV surface antigen, or a tetanus toxoid). In contrast, acellular whooping cough vaccines typically contain at least three *B.pertussis* proteins and the PREVNAR™ pneumococcal vaccine contains seven separate conjugated saccharide antigens. Other vaccines such as cellular pertussis vaccines, the measles vaccine, the inactivated polio vaccine (TPV) and meningococcal OMV vaccines are by their very nature complex mixtures of a large number of antigens. Whether protection can be elicited by a single antigen, a small number of defined antigens, or a complex mixture of undefined antigens, therefore depends on a number of factors.

The Immunogenic Polypeptide(s)

In some embodiments, the invention involves administration of at least one immunogenic polypeptide to subjects in order to provide protection against *Neisseria meningitidis* infection. These immunogenic polypeptides will generally include meningococcal amino acid sequences, such as amino acid sequences found in serogroup B strains, such as the sequenced MC58 strain [13].

A small number of defined antigens may be used. Rather than consisting of a single antigen, therefore, it is preferred that the composition of the invention comprises a mixture of 10 or fewer (e.g. 9, 8, 7, 6, 5, 4, 3, 2) purified antigens, and it is particularly preferred that the composition should not include complex or undefined mixtures of antigens e.g. it is preferred not to include outer membrane vesicles in the composition.

Preferred immunogenic polypeptides for use with the invention are those disclosed in reference 24: (1) a 'NadA' protein; (2) a '741' protein; (3) a '936' protein; (4) a '953' protein; and (5) a '287' protein. These antigens are referred to herein as the 'five basic antigens'. The invention may use 1, 2, 3, 4 or all 5 of these antigens.

NadA Protein

'NadA' (Neisserial adhesin A) from serogroup B of *N. meningitidis* is disclosed as protein '961' in reference 17 (SEQ IDs 2943 & 2944) and as 'NMB1994' in reference. 13 (see also GenBank accession numbers: 11352904 & 7227256). A detailed description of the protein can be found in reference 25. No corresponding protein was seen in the serogroup A genome [12, 25], but NadA$^+$ serogroup A strains have been reported since [25].

When used according to the present invention, NadA may take various forms. Preferred forms of NadA are truncation or deletion variants, such as those disclosed in references 21 to 23. In particular, NadA without its C-terminal membrane anchor is preferred (e.g. deletion of residues 351-405 for strain 2996 [SEQ ID NO: 1]), which is sometimes distinguished herein by the use of a 'C' superscript e.g. NadA(C). Expression of NadA without its membrane anchor domain (e.g. SEQ ID NO: 1) in *E. coli* results in secretion of the protein into the culture supernatant with concomitant removal of its 23 mer leader peptide (e.g. to leave a 327 mer for strain 2996 [SEQ ID NO: 2]). Polypeptides without their leader peptides are sometimes distinguished herein by the use of a 'NL' superscript e.g. NadA$^{(NL)}$ or NadA$^{(C)(NL)}$.

Preferred NadA sequences have 50% or more identity (e.g. 60%, 70%, 80%, 90%, 95%, 99% or more) to SEQ ID NO: 2. This includes NadA variants (e.g. allelic variants, homologs, orthologs, paralogs, mutants, etc.). Allelic forms of NadA are shown in FIG. 9 of reference 26.

Other preferred NadA sequences comprise at least n consecutive amino acids from SEQ ID NO: 1, wherein n is 7 or more (eg. 8, 10, 12, 14, 16, 18, 20, 25, 30, 35, 40, 50, 60, 70, 80, 90, 100, 150, 200, 250 or more). Preferred fragments comprise an epitope from NadA. Other preferred fragments lack one or more amino acids (e.g. 1, 2, 3, 4, 5, 6, 7, 8, 9, 10, 15, 20, 25 or more) from the C-terminus and/or the N-terminus of SEQ ID NO: 1 (e.g. NadA$^{(C)}$, NadA$^{(NL)}$, NadA$^{(C)(NL)}$). Where N-terminus residues are deleted, it is preferred that the deletion should not remove the ability of NadA to adhere to human epithelial cells. A preferred fragment of SEQ ID NO: 1 is SEQ ID NO: 2.

NadA is preferably used in an oligomeric form (e.g. in trimeric form).

741 Protein

'741' protein from serogroup B is disclosed in reference 17 (SEQ IDs 2535 & 2536) and as 'NMB1870' in reference 13 (see also GenBank accession number GI:7227128). The corresponding protein in serogroup A [12] has GenBank accession number 7379322. 741 is naturally a lipoprotein.

When used according to the present invention, 741 protein may take various forms. Preferred forms of 741 are truncation or deletion variants, such as those disclosed in references 21 to 23. In particular, the N-terminus of 741 may be deleted up to and including its poly-glycine sequence (i.e. deletion of residues 1 to 72 for strain MC58 [SEQ ID NO: 3]), which is sometimes distinguished herein by the use of a 'ΔG' prefix. This deletion can enhance expression. The deletion also removes 741's lipidation site.

Preferred 741 sequences have 50% or more identity (e.g. 60%, 70%, 80%, 90%, 95%, 99% or more) to SEQ ID NO: 3. This includes 741 variants (e.g. allelic variants, homologs, orthologs, paralogs, mutants, etc.). Allelic forms of 741 can be found in SEQ IDs 1 to 22 of reference 23, and in SEQ IDs 1 to 23 and 123-141 of reference 27. SEQ IDs 1-299 of reference 28 give further 741 sequences.

Other preferred 741 sequences comprise at least n consecutive amino acids from SEQ ID NO: 3, wherein n is 7 or more (eg. 8, 10, 12, 14, 16, 18, 20, 25, 30, 35, 40, 50, 60, 70, 80, 90, 100, 150, 200, 250 or more). Preferred fragments comprise an epitope from 741. Other preferred fragments lack one or more amino acids (e.g. 1, 2, 3, 4, 5, 6, 7, 8, 9, 10, 15, 20, 25 or more) from the C-terminus and/or the N-terminus of SEQ ID NO: 3.

Protein 741 is an extremely effective antigen for eliciting anti-meningococcal antibody responses, and it is expressed across all meningococcal serogroups. Phylogenetic analysis shows that the protein splits into two groups, and that one of these splits again to give three variants in total [29], and while serum raised against a given variant is bactericidal within the same variant group, it is not active against strains which express one of the other two variants i.e. there is intra-variant cross-protection, but not inter-variant cross-protection. For maximum cross-strain efficacy, therefore, it is preferred that a composition should include more than one variant of protein 741. An exemplary sequence from each variant is given in SEQ ID NOs: 10, 11 and 12 herein, starting with a N-terminal cysteine residue to which a lipid will be covalently attached in the lipoprotein form of 741.

It is therefore preferred that the composition should include at least two of: (1) a first protein, comprising an amino acid sequence having at least a% sequence identity to SEQ ID NO: 10 and/or comprising an amino acid sequence consisting of a fragment of at least x contiguous amino acids from SEQ ID NO: 10; (2) a second protein, comprising an amino acid sequence having at least b% sequence identity to SEQ ID NO: 11 and/or comprising an amino acid sequence consisting of a fragment of at least y contiguous amino acids from SEQ ID NO: 11; and (3) a third protein, comprising an amino acid sequence having at least c% sequence identity to SEQ ID NO: 12 and/or comprising an amino acid sequence consisting of a fragment of at least z contiguous amino acids from SEQ ID NO: 12.

The value of a is at least 85 e.g. 86, 87, 88, 89, 90, 91, 92, 93, 94, 95, 96, 97, 98, 99, 99.5, or more. The value of b is at least 85 e.g. 86, 87, 88, 89, 90, 91, 92, 93, 94, 95, 96, 97, 98, 99, 99.5, or more. The value of c is at least 85 e.g. 86, 87, 88, 89, 90, 91, 92, 93, 94, 95, 96, 97, 98, 99, 99.5, or more. The values of a, b and c are not intrinsically related to each other.

The value of x is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of y is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of z is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The values of x, y and z are not intrinsically related to each other.

It is preferred that any given 741 amino acid sequence will not fall into more than one of categories (1), (2) and (3). Any given 741 sequence will thus fall into only one of categories (1), (2) and (3). It is thus preferred that: protein (1) has less than i% sequence identity to protein (2); protein (1) has less than j% sequence identity to protein (3); and protein (2) has less than k% sequence identity to protein (3). The value of i is 60 or more (e.g. 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, etc.) and is at most a. The value of; is 60 or more (e.g. 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, etc.) arid is at most b. The value of k is 60 or more (e.g. 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, etc.) and is at most c. The values of i, j and k are not intrinsically related to each other.

936 Protein

'936' protein from serogroup B is disclosed in reference 17 (SEQ IDs 2883 & 2884) and as 'NMB2091' in reference 13 (see also GenBank accession number GI:7227353). The corresponding gene in serogroup A [12] has GenBank accession number 7379093.

When used according to the present invention, 936 protein may take various forms. Preferred forms of 936 are truncation or deletion variants, such as those disclosed in references 21 to 23. In particular, the N-terminus leader peptide of 936 may be deleted (i.e. deletion of residues 1 to 23 for strain MC58[SEQ ID NO: 4]) to give 936$^{(NL)}$.

Preferred 936 sequences have 50% or more identity (e.g. 60%, 70%, 80%, 90%, 95%, 99% or more) to SEQ ID NO: 4. This includes variants (e.g. allelic variants, homologs, orthologs, paralogs, mutants etc). Other preferred 936 sequences comprise at least n consecutive amino acids from SEQ ID NO: 4, wherein n is 7 or more (e.g. 8,10, 12, 14, 16, 18, 20, 25, 30, 35, 40, 50, 60, 70, 80, 90, 100, 150, 200, 250 or more), Preferred fragments comprise an epitope from 936. Other preferred fragments lack one or more amino acids (e.g. 1, 2, 3, 4, 5, 6, 7, 8, 9, 10, 15, 20, 25 or more) from the C-terminus and/or the N-terminus of SEQ ID NO: 4.

953 Protein

'953' protein from serogroup B is disclosed in reference 17 (SEQ IDs 2917 & 2918) and as 'NMB1030' in reference 13 (see also GenBank accession number GI:7226269). The corresponding protein in serogroup A [12] has GenBank accession number 7380108.

When used according to the present invention, 953 protein may take various forms. Preferred forms of 953 are truncation or deletion variants, such as those disclosed in references 21 to 23. In particular, the N-terminus leader peptide of 953 may be deleted (i.e. deletion of residues 1 to 19 for strain MC58[SEQ ID NO: 5]) to give 953.

Preferred 953 sequences have 50% or more identity (e.g. 60%, 70%, 80%, 90%, 95%, 99% or more) to SEQ ID NO: 5. This includes 953 variants (e.g. allelic variants, homologs, orthologs, paralogs, mutants, etc.). Allelic forms of 953 can be seen in FIG. 19 of reference 19.

Other preferred 953 sequences comprise at least n consecutive amino acids from SEQ ID NO: 5, wherein n is 7 or more (eg. 8, 10, 12, 14, 16, 18, 20, 25, 30, 35, 40, 50, 60, 70, 80, 90, 100, 150, 200, 250 or more). Preferred fragments comprise an epitope from 953. Other preferred fragments lack one or more amino acids (e.g. 1, 2, 3, 4, 5, 6, 7, 8, 9, 10, 15, 20, 25 or more) from the C-terminus and/or the N-terminus. of SEQ ID NO: 5.

287 Protein

'287' protein from serogroup B is disclosed in reference 17 (SEQ IDs 3103 & 3104), as 'NMB2132' in reference 13, and as 'GNA2132' in reference 20 (see also GenBank accession number GI:7227388). The corresponding protein in serogroup A [12], has GenBank accession number 7379057.

When used according to the present invention, 287 protein may take various forms. Preferred forms of 287 are truncation or deletion variants, such as those disclosed in references 21 to 23. In particular, the N-terminus of 287 may be deleted up to and including its poly-glycine sequence (i.e. deletion of residues 1 to 24 for strain MC58 [SEQ ID NO: 6]), which is sometimes distinguished herein by the use of a 'ΔG' prefix. This deletion can enhance expression.

Preferred 287 sequences have 50% or more identity (e.g. 60%, 70%, 80%, 90%, 95%, 99% or more) to SEQ ID NO: 6. This includes 287 variants (e.g. allelic variants, homologs, orthologs, paralogs, mutants, etc.). Allelic forms of 287 can be seen in FIGS. 5 and 15 of reference 19, and in example 13 and FIG. 21 of reference 17 (SEQ IDs 3179 to 3184).

Other preferred 287 sequences comprise at least n consecutive amino acids from SEQ ID 6, wherein n is 7 or more (eg. 8, 10, 12, 14, 16, 18, 20, 25, 30, 35, 40, 50, 60, 70, 80, 90, 100, 150, 200, 250 or more). Preferred fragments comprise an epitope from 287. Other preferred fragments lack one or more amino acids (e.g. 1, 2, 3, 4, 5, 6, 7, 8, 9, 10, 15, 20, 25 or more) from the C-terminus and/or the N-terminus of SEQ ID NO: 6.

Fusion Proteins

The five antigens may be present in the composition as five separate polypeptides, but it is preferred that at least two of the antigens are expressed as a single polypeptide chain (a 'hybrid' protein [refs. 21 to 24]) e.g. such that the five antigens form fewer than five polypeptides. Hybrid proteins offer two principal advantages: first, a protein that may be unstable or poorly expressed on its own can be assisted by adding a suitable hybrid partner that overcomes the problem; second, commercial manufacture is simplified as only one expression and purification need be employed in order to produce two separately-useful proteins.

A hybrid protein included in a composition of the invention may comprise two or more (i.e. 2, 3, 4 or 5) of the five basic antigens. Hybrids consisting of two of the five basic antigens are preferred.

Within the combination of five basic antigens, an antigen may be present in more than one hybrid protein and/or as a non-hybrid protein. It is preferred, however, that an antigen is present either as a hybrid or as a non-hybrid, but not as both, although it may be useful to include protein 741 both as a hybrid and a non-hybrid (preferably lipoprotein) antigen, particularly where more than one variant of 741 is used.

Two-antigen hybrids for use in the invention comprise: NadA & 741; NadA & 936; NadA & 953; NadA & 287; 741 & 936; 741 & 953; 741 & 287; 936 & 953; 936 & 287; 953 & 287. Preferred two-antigen hybrids comprise: 741 & 936; 953 & 287. See further details in reference 24.

Hybrid proteins can be represented by the formula $NH_2$-A-[-X-L-]$_n$-B—COOH, wherein: X is an amino acid sequence of one of the five basic antigens; L is an optional linker amino acid sequence; A is an optional N-terminal amino acid sequence; B is an optional C-terminal amino acid sequence; and n is 2, 3, 4 or 5.

If a -X- moiety has a leader peptide sequence in its wild-type form, this may be included or omitted in the hybrid protein. In some embodiments, the leader peptides will be deleted except for that of the -X- moiety located at the N-terminus of the hybrid protein i.e. the leader peptide of $X_1$ will be retained, but the leader peptides of $X_2 \ldots X_n$ will be omitted. This is equivalent to deleting all leader peptides and using the leader peptide of $X_1$ as moiety -A-.

For each n instances of [-X-L-], linker amino acid sequence -L- may be present or absent. For instance, when n=2 the hybrid may be $NH_2$-$X_1$-$L_1$-$X_2$—COOH, $NH_2$-$X_1$-$X_2$—COOH, $NH_2$-$X_1$-$L_1$-$X_2$—COOH, $NH_2$-$X_1$-$x_2$-$L_2$—COOH, etc. Linker amino acid sequence(s) -L- will typically be short (e.g. 20 or fewer amino acids i.e. 19, 18, 17, 16, 15, 14, 13, 12, 11, 10, 9, 8, 7, 6, 5, 4, 3, 2, 1). Examples comprise short peptide sequences which facilitate cloning, poly-glycine linkers (i.e. comprising $Gly_n$ where n=2, 3, 4, 5, 6, 7, 8, 9, 10 or more), and histidine tags (i.e. $His_n$ where n=3, 4, 5, 6, 7, 8, 9, 10 or more). Other suitable linker amino acid sequences will be apparent to those skilled in the art. A useful linker is GSGGGG (SEQ ID NO: 9), with the Gly-Ser dipeptide being formed from a BamHI restriction site, thus aiding cloning and manipulation, and the $(Gly)_4$ tetrapeptide being a typical poly-glycine linker. If $X_{n+1}$ is a ΔG protein and $L_n$ is a glycine linker, this may be equivalent to $X_{n+1}$ not being a ΔG protein and $L_n$ being absent.

-A- is an optional N-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. histidine tags i.e. $His_n$ where n=3, 4, 5, 6, 7, 8, 9, 10 or more). Other suitable N-terminal amino acid sequences will be apparent to those skilled in the art. If $X_1$ lacks its own N-terminus methionine, -A- is preferably an oligopeptide (e.g. with 1, 2, 3, 4, 5, 6, 7 or 8 amino acids) which provides a N-terminus methionine.

-B- is an optional C-terminal amino acid sequence. This will typically be short (e.g. 40 or fewer amino, acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate, cloning or purification (e.g. comprising histidine tags i.e. $His_n$ where n=3, 4, 5, 6, 7, 8, 9, 10 or more), or sequences which enhance protein stability. Other suitable C-terminal amino acid sequences will be apparent to those skilled in the art.

Most preferably, n is 2. Two preferred proteins of this type are: $X_1$ is a 936 and $X_2$ is a 741; $X_1$ is a 287 and $X_2$ is a 953.

Two particularly preferred hybrid proteins of the invention are as follows:

| n | A | $X_1$ | $L_1$ | $X_2$ | $L_2$ | B | [SEQ ID NO:] |
|---|---|---|---|---|---|---|---|
| 2 | M A | ΔG287 | SEQ ID NO: 9 | 953$^{(NL)}$ | — | — | 7 |
| 2 | M | 936$^{(NL)}$ | SEQ ID NO: 9 | ΔG741 | — | — | 8 |

These two proteins may be used in combination with NadA (particularly with SEQ ID NO: 2) [24].

Mixtures excluding OMVs and/or excluding lipooligosaccharide are preferred.

Outer Membrane Vesicles

As an alternative to using purified polypeptide antigens, the invention may employ preparations of *N. meningitidis* microvesicles [30], 'native OMVs' [31], blebs or outer membrane vesicles [e.g. refs. 32 to 37 etc.]. All of these various preparations are referred to herein under the general term 'OMVs'.

In some embodiments, OMVs may be prepared from bacteria that have been genetically manipulated [38-41] e.g. to increase immunogenicity (e.g. hyper-express immunogens), to reduce toxicity, to inhibit capsular polysaccharide synthesis, to down-regulate or knockout PorA expression, to down-regulate or knockout lgtB expression [42], etc. They may be prepared from hyperblebbing strains [43-46]. Vesicles from a non-pathogenic *Neisseria* may be included [47]. OMVs may be prepared without the use of detergents [48,49]. They may express non-Neisserial proteins on their surface They may be LPS-depleted. They may retain lipooligosaccharide as an important antigen [42,51]. They may be mixed with recombinant antigens [32,52]. They may be treated to reduce phase variability of lipooligosaccharide immunotype [53]. Mixtures of OMVs may be used [30] including mixtures from different serotypes and/or serosubtypes [30,54].

Vesicles from bacteria with different class I outer membrane protein subtypes may be used e.g. six different subtypes [55,56] using two different genetically-engineered vesicle populations each displaying three subtypes, or nine different subtypes, using three different genetically-engineered vesicle populations each displaying three subtypes, etc. Useful subtypes include: P1.7,16; P1.5-1,2-2; P1.19,15-1; P1.5-2,10; P1.12-1,13; P1.7-2,4;P1.22,14; P1.7-1,1; P1.18-1,3,6.

Result of Immunisation

The result of the immunisation will be generation of antibodies in the subject that (a) recognise the immunogenic polypeptide and (b) are protective against infection by multiple meningococcal serotypes. A typical result of immunisation will be the generation of an antibody response that is bactericidal against at least serogroup Y meningococcus, and more typically against each of serogroups A, B, C, W135 and Y.

A preferred result is effective immunisation against: (a) serogroups Y and A; (b) serogroups Y and B; (c) serogroups Y and C; (d) serogroups Y and W135; etc. Immunisation against at least serogroups A, B, C and Y is preferred. Protection may also be provided against other (non-pathogenic) serogroups e.g. H, I, K, L, X, Z, 29E, etc. Protection may also be provided against other *Neisseria* species e.g. lactamica, gonorrhoeae, cinerea, etc.

After immunisation, a serum preferably has a bactericidal titre of at least 1024 (e.g. $2^{10}$, $2^{11}$, $2^{12}$, $2^{13}$, $2^{14}$, $2^{15}$, $2^{16}$, $2^{17}$, $2^{18}$ or higher, preferably at least $2^{14}$) i.e. the serum is able to kill at least 50% of test bacteria of a particular strain when diluted 1/1024, as described in reference 20.

Serogroups and Strains

The methods and uses of the invention are preferably for immunising a subject against infection by serogroup Y and also against at least one of serogroups A, B, C and W135.

Preferred proteins of the invention comprise an amino acid sequence found in *N. meningitidis* serogroup B. Within serogroup B, preferred strains are 2996, MC58, 95N477, and 394/98. Strain 394/98 is sometimes referred to herein as 'NZ', as it is a New Zealand strain.

Protein 287 is preferably from strain 2996 or, more preferably, from strain 394/98.

Protein 741 is preferably from serogroup B strains MC58, 2996, 394/98, or 95N477, or from serogroup C strain 90/18311. Strain MC58 is more preferred.

Proteins 936, 953 and NadA are preferably from strain 2996.

Strains may be indicated as a subscript e.g. $741_{mc58}$ is protein 741 from strain MC58. Unless otherwise stated, proteins mentioned herein (e.g. with no subscript) are from *N.meningitidis* strain 2996, which can be taken as a 'reference' strain. It will be appreciated, however, that the invention is not in general limited by strain. As mentioned above, general references to a protein (e.g. '287', '919' etc.) may be taken to include that protein from any strain. This will typically have sequence identity to 2996 of 90% or more (eg. 91%, 92%, 93%, 94%, 95%, 96%, 97%, 98%, 99% or more).

Where a composition includes a particular protein antigen (e.g. 741 or 287), the composition can include that antigen in more than one variant form e.g. the same protein, but from more than one strain. These proteins may be included as tandem or separate proteins.

Where hybrid proteins are used, the individual antigens within the hybrid (i.e. individual -X- moieties) may be from one or more strains. Where n=2, for instance, $X_2$ may be from the same strain as $X_1$ or from a different strain. Where n=3, the strains might be (i) $X_1=X_2=X_3$ (ii) $X_1=X_2\neq X_3$ (iii) $X_1\neq X_2=X_3$ (iv) $X_1\neq X_2\neq X_3$ or (v) $X_1=X_3\neq X_2$, etc Hypervirulent Lineages and Bactericidal Antibody Responses In general, compositions of the invention are able to induce serum bactericidal antibody responses after being administered to a subject. These responses are conveniently measured in mice and are a standard indicator of vaccine efficacy [e.g. see end-note 14 of reference 20]. Serum bactericidal activity (SBA) measures bacterial killing mediated by complement, and can be assayed using human or baby rabbit complement. WHO standards require a vaccine to induce at least a 4-fold rise in SBA in more than 90% of recipients.

Rather than offering narrow protection, compositions of the invention can induce bactericidal antibody responses against more than one serogroup of meningococcus. Within serogroups, compositions may induce antibody responses against more than one hypervirulent lineage. In particular, they can induce bactericidal responses against two or three of the following three hypervirulent lineages: (i) cluster A4; (ii) ET5 complex; and (iii) lineage 3. They may additionally induce bactericidal antibody responses against one or more of hypervirulent lineages subgroup I, subgroup III, subgroup IV-1 or ET-37 complex, and against other lineages e.g. hyperinvasive lineages. However, compositions need not induce bactericidal antibodies against each and every strain of a particular hypervirulent lineage.

Preferred compositions can induce bactericidal responses against: (a) strain 860800, ES13822, ES15085 and/or ES14487 of serogroup Y meningococcus; (b) strain F6124 of serogroup A meningococcus; (c) strain LPN17592 of serogroup W135 meningococcus; (d) strain C11 of serogroup C meningococcus; (e) within serogroup B meningococcus: (i) from cluster A4, strain. 961-5945 (B:2b:P1.21, 16) and/or strain G2136 (B:-); (ii) from ET-5 complex, strain MC58(B:15:P1.7,16b) and/or strain 44/76 (B:15:P1.7, 16); (iii) from lineage 3, strain 394/98 (B:4:P1.4) and/or strain BZ198 (B:NT:-).

Serogroup Y strain 860800 is seen in row 29 of reference 1, and in reference 57. Serogroup A strain F6124 is seen in references 20, 57 & 58. Serogroup C strain C11 is one of the reference strains disclosed in ref. 59. Serogroup B strains 961-5945 and G2136 are both *Neisseria* MLST reference strains [ids 638 & 1002 in ref. 60]. Strain MC58 is widely available (e.g. ATCC BAA-335) and was the strain sequenced in reference 13. Strain 44/76 has been widely used and characterised (e.g. ref. 61) and is one of the *Neisseria* MLST reference strains [id 237 in ref. 60; row 32 of Table 2 in ref. 1]. Strain 394/98 was originally isolated in New Zealand in 1998, and there have been several published studies using this strain (e.g. refs. 62 & 63). Strain BZ198 is another MLST reference strain [id 409 in ref. 60; row 41 of Table 2 in ref. 1].

Immunogenic Compositions and Medicaments

Compositions of the invention are immunogenic, and are more preferably vaccine compositions. Vaccines according to the invention may either be prophylactic (i.e. to prevent infection) or therapeutic (i.e. to treat infection), but will typically be prophylactic.

The pH of the composition is preferably between 6 and 8, preferably about 7. Stable pH may be maintained by the use of a buffer. Where a composition comprises an aluminium hydroxide salt, it is preferred to use a histidine buffer [64]. The composition may be sterile and/or pyrogen-free. Compositions of the invention may be isotonic with respect to humans.

Compositions may be presented in vials, or they may be presented in ready-filled syringes. The syringes may be supplied with or without needles. A syringe will include a single dose of the composition, whereas a vial may include a single dose or multiple doses. Injectable compositions will usually be liquid solutions or suspensions. As an alternative, they may be presented in solid form (e.g. freeze-dried) for solution or suspension in liquid vehicles prior to injection.

Compositions of the invention may be packaged in unit dose form or in multiple dose form. For multiple dose forms, vials are preferred to pre-filled syringes. Effective dosage volumes can be routinely established, but a typical human dose of the composition for injection has a volume of 0.5 ml.

Where a composition of the invention is to be prepared extemporaneously prior to use (e.g. where a component is presented in lyophilised form) and is presented as a kit, the kit may comprise two vials, or it may comprise one ready-filled syringe and one vial, with the contents of the syringe being used to reactivate the contents of the vial prior to injection.

Immunisation of the invention is in a mammal, preferably in a human. Where the vaccine is for prophylactic use, the human is preferably a child (e.g. a toddler or infant); where the vaccine is for therapeutic use, the human is preferably an adult. A vaccine intended for children may also be administered to adults e.g. to assess safety, dosage, immunogenicity, etc.

These uses and methods are preferably for the prevention and/or treatment of a disease caused by a *Neisseria* (e.g. meningitis, septicaemia, bacteremia, gonorrhoea etc.). The prevention and/or treatment of bacterial or meningococcal meningitis is preferred.

One way of checking efficacy of therapeutic treatment involves monitoring Neisserial infection after administration of the composition of the invention. One way of checking efficacy of prophylactic treatment involves monitoring immune responses against administered antigens. Immunogenicity of compositions of the invention can be determined by administering them to test subjects (e.g. children 12-16 months age, or animal models [65]) and then determining standard parameters including serum bactericidal antibodies (SBA) and ELISA titres (GMT) of total and high-avidity IgG. These immune responses will generally be determined around 4 weeks after administration of the composition, and compared to values determined before administration of the composition. A SBA increase of at least 4-fold or 8-fold is preferred. Where more than one dose of the composition is administered, more than one post-administration determination may be made.

Preferred compositions of the invention can confer an antibody titre in a patient that is superior to the criterion for seroprotection for each antigenic component for an acceptable percentage of human subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

Compositions will, generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is 0.5 ml.

The invention may be used to elicit systemic and/or mucosal immunity.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

Neisserial infections affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition). The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as spray, drops, gel or powder [e.g. refs 66 & 67]. Success with nasal administration of pneumococcal saccharides [68,69], pneumococcal polypeptides [70], Hib saccharides [71], MenC saccharides [72], and mixtures of Hib and MenC saccharide conjugates [73] has been reported.

Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials, and a typical quantity of each meningococcal saccharide antigen per dose is between 1 µg and 20 µg e.g. about 1 µg, about 2.5 µg, about 4 µg, about 5 µg, or about 10 µg (expressed as saccharide).

Further Non-antigen Components of the Composition

The composition of the invention will typically, in addition to the components mentioned above, comprise one or more 'pharmaceutically acceptable carriers', which include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose [74], trehalose [75], lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present Sterile pyrogen-free, phosphate-buffered physiologic saline is a typical carrier. A thorough discussion of pharmaceutical acceptable excipients is available in reference 76.

Compositions of the invention may include an antimicrobial, particularly when packaged in multiple dose format.

Compositions of the invention may comprise detergent e.g. a TWEEN (™) (polysorbate), such as TWEEN 80 (™). Detergents are generally present at low levels e.g. <0.01%.

Compositions of the invention may include sodium salts (e.g. sodium chloride) to give tonicity. A concentration of 10±2 mg/ml NaCl is typical.

Compositions of the invention will generally include a buffer. A phosphate buffer is typical.

Compositions of the invention may comprise a sugar alcohol (e.g. mannitol) or a disaccharide (e.g. sucrose or trehalose) e.g. at around 15-30 mg/ml (e.g. 25 mg/ml), particularly if they are to be lyophilised or if they include material which has been reconstituted from lyophilised material. The pH of a composition for lyophilisation may be adjusted to around 6.1 prior to lyophilisation.

Vaccines of the invention may be administered in conjunction with other immunoregulatory agents. In particular, compositions will usually include an adjuvant. Adjuvants which may be used in compositions of the invention include, but are not limited to:

A. Mineral-containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref. 77], or mixtures of different mineral compounds, with the compounds taking any suitable form (e.g. gel, crystalline, amorphous, etc.), and with adsorption being preferred. The mineral containing compositions may also be formulated as a particle of metal salt [78].

Aluminium phosphates are particularly preferred, particularly in compositions which include a *H.influenzae* saccharide antigen, and a typical adjuvant is amorphous aluminium hydroxyphosphate with $PO_4/Al$ molar ratio between 0.84 and 0.92, included at 0.6 mg $Al^{3+}$/ml. Adsorption with a low dose of aluminium phosphate may be used e.g. between 50 and 100 μg Al³⁺ per conjugate per dose. Where there is more than one conjugate in a composition, not all conjugates need to be adsorbed.

B. Oil Emulsions

Oil emulsion compositions suitable for use as adjuvants in the invention include squalene-water emulsions, such as MF59 (™) [Chapter 10 of ref. 77; see also ref. 79] (5% Squalene,0.5% TWEEN 80 (™), and 0.5% SPAN 85 (™), formulated into submicron particles using a microfluidizer). Complete Freund's adjuvant (CFA) and incomplete Freund's adjuvant (IFA) may also be used.

C. Saponin formulations [Chapter 22 of ref. 77]

Saponin formulations may also be used as adjuvants in the invention. Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 80. Saponin formulations may also comprise a sterol, such as cholesterol [81].

Combinations of saponins and cholesterols can be used to form unique particles called immunostimulating complexs (ISCOMs) [chapter 23 of ref. 77]. ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 81-83. Optionally, the ISCOMS may be devoid of additional detergent [84]

A review of the development of saponin based adjuvants can be found in refs. 85 & 86.

D. Virosomes and Virus-like Particles

Virosomes and-virus-like particles (VLPs) can also be used as adjuvants in the invention. These, structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in refs. 87-92. Virosomes are discussed further in, for example, ref. 93.

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 94. Such "small particles" of 3dMPL are small enough to be sterile filtered through a 0.22 μm membrane [94]. Other non-toxic LPS derivatives include monophosphoryl lipid A mimics, such as aminoalkyl glucosaminide phosphate derivatives e.g. RC-529 [95,96].

Lipid A derivatives include derivatives of lipid A from *Escherichia coli* such as OM-174. OM-174 is described for example in refs. 97 & 98.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 99, 100 and 101 disclose possible analog substitutions e.g. replacement of guanosine with 2'-deoxy-7-deazaguanosine. The adjuvant effect of CpG oligonucleotides is further discussed in refs. 102-107.

The CpG sequence may be directed to TLR9, such as the motif GTCGTT or TTCGTT [108]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 109-111. Preferably, the CpG is a CpG-A ODN.

Preferably, the CpG oligqnucleotide is constructed so that the 5' end is accessible for receptor recognition. Optionally, two CpG oligonucleotide sequences may be attached at their 3' ends to form "immunomers". See, for example, refs. 108 & 112-114.

Bacterial ADP-ribosylating toxins and detoxified derivatives thereof may be used as adjuvants in the invention. Preferably, the protein is derived from *E.coli* (*E.coli* heat labile enterotoxin "LT"), cholera ("CT" ), or pertussis ("PT"). The use of detoxified ADP-ribosylating toxins as mucosal adjuvants is described in ref. 115 and as parenteral adjuvants in ref. 116. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivaties thereof, particularly LT-K63 and LT-R72, as adjuvants can be found in refs. 117-124. Numerical reference for amino acid substitutions is preferably based on the alignments of the A and B subunits of ADP-ribosylating toxins set forth in ref. 125, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12. [126], etc.) [127], interferons (e.g. interferon-γ), macrophage colony stimulating factor, and tumor necrosis factor.

G. Bioadhesives and Mucoadhesives

Bioadhesives and mucoadhesives may also be used as adjuvants in the invention. Suitable bioadhesives include esterified hyaluronic acid microspheres [128] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [129].

H. Microparticles

Microparticles may also be used as adjuvants in the invention. Microparticles (i.e. a particle of ~100 nm to ~150 µm in diameter, more preferably ~200 nm to ~30 µm in diameter, and most preferably ~500 nm to ~10 µm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of ref. 77)

Examples of liposome formulations suitable for use as adjuvants are described in refs. 130-132.

J. Polyoxyethylene Ether and Polvoxyethylene Ester Formulations

Adjuvants suitable for use in the invention include polyoxyethylene ethers and polyoxyethylene esters [133]. Such formulations further include polyoxyethylene sorbitan ester surfactants in combination with an pctoxynol [134] as well as polyoxyemyleneralkyi ethers or ester surfactants in combination with at least one additional non-ionic surfactant such as an octoxynol [135]. Preferred polyoxyethylene ethers are selected from the following group: polyoxyethylene-9-lauryl ether (laureth 9), polyoxyethylene-9-steoryl ether, polyoxytheylene-8-steoryl. ether, polyoxyethylene-4-lauryl ether, polyoxyethylene-35-lauryl ether, and polyoxyethylene-23-lauryl ether.

K. Polyphosphazene (PCPP)

PCPP formulations are described, for example, in refs. 136 and 137.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutammyl-L-alanine-2-(1'-2'-dipalmitoyl-sn-glycero-3-hydroxyphosphoryloxy)-ethylamine MTP-PE).

M. Imidazoquinolone Compounds

Examples of imidazoquinolone compounds suitable for use adjuvants in the invention include Imiquamod and its homologues (e,g. "Resiquimod 3M"), described further in refs. 138 and 139.

The invention may also comprise combinations of aspects of one or more of the adjuvants identified above. For example, the following adjuvant compositions may be used in the invention: (1) a saponin and an oil-in-water emulsion [140]; (2) a saponin (e.g. QS21) +a non-toxic LPS derivative (e.g. 3dMPL) [141]; (3) a saponin (e.g. QS21) +a non-toxic LPS derivative (e.g. 3dMPL) +a cholesterol; (4) a saponin (e.g. QS21) +3dMPL +IL-12 (optionally +a sterol) [142]; (5) combinations of 3dMPL with, for example, QS21 and/or oil-in-water emulsions [143]; (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% TWEEN 80 (™), and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of ref. 77.

The use of an aluminium hydroxide or aluminium phosphate adjuvant is particularly preferred, and antigens are generally adsorbed to these salts. Aluminium hydroxide is preferably avoided as an adjuvant if the composition includes a Hib antigen. Where an aluminium phosphate it used and desired not to adsorb an antigen to the adjuvant, this is favoured by including free-phosphate ions, in solution (e.g. by the use of a phosphate buffer). Prevention of adsorption can also be achieved by selecting the correct pH during antigen/adjuvant mixing, an adjuvant with an appropriate point of zero charge, and an appropriate order of mixing for different antigens in a composition [144].

Calcium phosphate is another preferred adjuvant.

Further Antigens

Compositions of the invention contain five basic meningococcal protein antigens. They may also include further antigens, although it may contain no meningococcal protein antigens other than the five basic antigens. Further antigens for inclusion may be, for example:

a saccharide antigen from *Haemophilus influenzae* B.

a saccharide antigen from *N. meningitidis* serogroup A, C, W135 and/or Y, such as the saccharide disclosed in ref. 5 from serogroup C or the saccharides of ref. 8 (see below).

a saccharide antigen from *Streptococcus pneumoniae* [e.g. 180, 181 182].

an antigen from hepatitis A virus, such as inactivated virus [e.g. 145, 146].

an antigen from hepatitis B virus, such as the surface and/or core antigens [e.g. 146, 147].

a diphtheria antigen, such as a diphtheria toxoid [e.g. chapter 3 of ref. 148] e.g. the $CRM_{197}$ mutant [e.g. 149].

a tetanus antigen, such as a tetanus toxoid [e.g. chapter 4 of ref. 148].

an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 150 & 151]. Cellular pertussis antigen may be used.

an outer-membrane vesicle (OMV) preparation from *N. meningitidis* serogroup B, such as those disclosed in refs. 34, 35, 37, 152, etc.

polio antigen(s) [e.g. 153, 154] such as OPV or, preferably, IPV.

The composition may comprise one or more of these further antigens. Antigens will typically be present at a concentration of at least 1 µg/ml each. In general, the concentration of any given antigen will be sufficient to elicit an immune response against that antigen. It is preferred that the protective efficacy of individual saccharide antigens is not removed by combining them, although actual immunogenicity (e.g. ELISA titres) may be reduced.

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. Such DTP combinations can be used to reconstitute lyophilised conjugates.

Where a saccharide or carbohydrate antigen is used, it is preferably conjugated to a carrier protein in order to enhance immunogenicity (see below).

Toxic protein antigens may be detoxified where necessary (e.g. detoxification of pertussis toxin by chemical and/or genetic means [151]).

As an alternative to using protein antigens in the composition of the invention, nucleic acid encoding the antigen may be used [e.g. refs. 155 to 163]. Protein components of the compositions of the invention may thus be replaced by nucleic acid (preferably DNA e.g. in the form of a plasmid) that encodes the protein. Similarly, compositions of the invention may comprise proteins which mimic saccharide antigens e.g. mimotopes [164] or anti-idiotype antibodies. These may replace individual saccharide components, or may supplement them. As an example, the vaccine may comprise a peptide mimic of the MenC [165] or the MenA [166] capsular polysaccharide in place of the saccharide itself.

Particularly preferred compositions of the invention include either or both of: (a) a saccharide antigen from *Haemophilus influenzae* type B; and/or (b) an antigen from *Streptococcus pneumoniae*. They may also include saccharide antigens from meningococcus serogroups Y, W135, C and A, except that the saccharide from a given serogroup may be included only where the polypeptide(s) and/or OMVs are not for providing protection against that serogroup.

Haemophilus Influenzae Type B

Where the composition includes a *H. influenzae* type B antigen, it will typically be a Hib capsular saccharide antigen. Saccharide antigens from *H. influenzae* b are well known.

Advantageously, the Hib saccharide is covalently conjugated to a carrier protein, in order to enhance its immunogenicity, especially in children. The preparation of polysaccharide conjugates in general, and of the Hib capsular polysaccharide in particular, is well documented [e.g. references 167 to 175 etc.]. The invention may use any suitable Hib conjugate. Suitable carrier proteins are described below, and preferred carriers for Hib saccharides are $CRM_{197}$ ('HbOC'), tetanus toxoid ('PRP-T') and the outer membrane complex of *N. meningitidis* ('PRP-OMP').

The saccharide moiety of the conjugate may be a polysaccharide (e.g. full-length polyribosylribitol phosphate (PRP)), but it is preferred to hydrolyse polysaccharides to form oligosaccharides (e.g. MW from ~1 to ~5 kDa).

A preferred conjugate comprises a Hib oligosaccharide covalently linked to $CRM_{197}$ via an adipic acid linker [176, 177]. Tetanus toxoid is also a preferred carrier.

Administration of the Hib antigen preferably results in an anti-PRP antibody concentration of ≥0.15 µg/ml, and more preferably ≥1 µg/ml.

Compositions of the invention may comprise more than one Hib antigen.

Where a composition includes a Hib saccharide; antigen, it is-preferred that it does not also include an aluminium hydroxide adjuvant. If the cbmposition includes an aluminium phosphate adjuvant then the Hib antigen may be adsorbed to the adjuvant [178] or it may be non-adsorbed [179].

Hib antigens may be lyophilised e.g. together with meningococcal antigens.

*Streptococcus pneumoniae*

Where the composition includes a *S. pneumoniae* antigen, it will typically be a capsular saccharide antigen which is preferably conjugated to a carrier protein [e.g. refs. 180 to 182]. It is preferred to include saccharides from more than one serotype of *S. pneumoniae*. For example, mixtures of polysaccharides from 23 different serotype are widely used, as are conjugate vaccines with polysaccharides from between 5 and 11 different serotypes [183]. For example, PREVNAR™ [184] contains, antigens from seven serotypes (4, 6B, 9V, 14, 18C, 19F, and 23F) with each saccharide individually conjugated to $CRM_{197}$ by reductive amination, with 2 µg of each saccharide per 0.5 ml dose (4 µg of serotype 6B), and with conjugates adsorbed on an aluminium phosphate adjuvant. Compositions of the invention preferably include at least serotypes 6B, 14, 19F and 23F. Conjugates may be adsorbed onto an aluminium phosphate.

As an alternative to using saccharide antigens from pneumococcus, the composition may include one or more polypeptide antigens. Genome sequences for several strains of pneumococcus are available [185,186] and can be subjected, to reverse vaccinology [187-190] to identify suitable polypeptide antigens [191,192]. For example, the composition may include one or more of the following antigens: PhtA, PhtD, PhtB, PhtE, SpsA, LytB, LytC, LytA, Sp125, Sp101, Sp128, Sp130 and Sp130, as defined in reference 193. The composition may include more than one (e.g. 2, 3, 4, 5, 6, 7, 8, 9 10, 11, 12, 13 or 14) of these antigens.

In some embodiments, the composition may include both saccharide and polypeptide antigens from pneumococcus. These may be used in simple admixture, or the pneumococcal saccharide antigen may be conjugated to a pneumococcal protein. Suitable carrier proteins for such embodiments include the antigens listed in the previous paragraph [193].

Pneumococcal antigens may be lyophilised e.g. together with meningococcal and/or Hib antigens.

Meningococcus serogroups Y. W135, C and A

As mentioned above, polysaccharide vaccines against serogroups A, C, W135 & Y has been known for many years. These vaccines (MENCEVAX ACWY™ and MENOMUNE™) are based on the organisms' capsular polysaccharides and, although they are effective in adolescents and adults, they give a poor immune response and short duration of protection, and they cannot be used in infants.

In contrast to the unconjugated polysaccharide antigens in these vaccines, the recently-approved serogroup C vaccines (MENJUGATE™. [4], Meningitec™ and NEISVAC-C™) include conjugated saccharides. MENJUGATE™ and MENINGITEC™ have oligosaccharide antigens conjugated to a $CRM_{197}$ carrier, whereas NEISVAC-C™ uses the complete polysaccharide (de-O-acetylated) conjugated to a tetanus toxoid carrier.

Compositions of the present invention preferably include capsular saccharide antigens from one or more of meningococcus serogroups Y, W135, C and A, wherein the antigens are conjugated to carrier protein(s) and are optionally oligosaccharides. Meningococcal capsular polysaccharides and their conjugates can be prepared as described in references 7 and 8.

A typical quantity of each meningococcal saccharide antigen per dose is between 1 µg and 20 µg e.g. about 1 µg, about 2.5 µg, about 4 µg, about 5 µg, or about 10 µg (expressed as saccharide).

Where a mixture comprises capsular saccharides from both serogroups A and C, the ratio (w/w) of MenA saccharide:MenC saccharide may be greater than 1 (e.g. 2:1, 3:1, 4:1, 5:1, 10:1 or higher). Where a mixture comprises capsular saccharides from serogroup Y and one or both of serogroups C and W135, the ratio (w/w) of MenY saccharide:MenW135 saccharide may be greater than 1 (e.g. 2:1, 3:1, 4:1, 5:1, 10:1 or higher) and/or that the ratio (w/w) of MenY saccharide:MenC saccharide may be less than 1 (e.g. 1:2, 1:3, 1:4, 1:5, or lower). Preferred ratios (w/w) for saccharides from serogroups A:C:W135:Y are: 1:1:1:1; 1:1:1:2; 2:1:1:1; 4:2:1:1; 8:4:2:1; 4:2:1:2; 8:4:1:2; 4:2:2:1; 2:2:1:1; 4:4:2:1; 2:2:1:2; 4:4:1:2; and 2:2:2:1. Preferred ratios (w/w) for saccharides from serogroups C:W135:Y are: 1:1:1; 1:1:2; 1:1:1; 2:1:1; 4:2:1; 2:1:2; 4:1:2; 2:2:1; and 2:1:1. Using a substantially equal mass of each saccharide is preferred.

Capsular saccharides will generally be used in the form of oligosaccharides. These are conveniently formed by fragmentation of purified capsular polysaccharide (e.g. by hydrolysis), which will usually be followed by purification of the fragments of the desired size.

Fragmentation of polysaccharides is preferably performed to give a final average degree of polymerisation (DP) in the oligosaccharide of less than 30 (e.g. between 10 and 20, preferably around 10 for serogroup A; between 15 and 25 for serogroups W135 and Y, preferably around 15-20; between 12 and 22 for serogroup C; etc.). DP can conveniently be measured by ion exchange chromatography or by colorimetric assays [194].

If hydrolysis is performed, the hydrolysate will generally be sized in order to remove short-length oligosaccharides [195]. This can be achieved in various ways, such as ultrafiltration followed by ion-exchange chromatography. Oligosaccharides with a degree of polymerisation of less than or equal to about 6 are preferably removed for serogroup A, and those less than around 4 are preferably removed for serogroups W135 and Y.

Preferred MenC saccharide antigens are disclosed in reference 5, as used in MENJUGATE™.

Saccharides are preferably prepared separately (including any fragmentation, conjugation, modification, etc.) and then admixed to give a composition of the invention.

Where the composition comprises capsular, saccharide from serogroup A, however, it is preferred that the serogroup A saccharide is not combined with the other saccharide(s) until shortly before use, in order to minimise the potential for hydrolysis. This can conveniently be achieved by having the serogroup A component (typically together with appropriate excipients) in lyophilised form and the other serogroup components) in liquid form (also with appropriate excipients), with the liquid components being used to reconstitute the lyophilised MenA component when ready for use. Where an aluminium salt adjuvant is used, it is preferred to include the adjuvant in the vial containing the with the liquid vaccine, and to lyophilise the MenA component without adjuvant. A composition of the invention may thus be prepared from a kit comprising: (a) capsular saccharide from *N. meningitidis* serogroup A, in lyophilised form; and (b) the further antigens from the composition, in liquid form.

Covalent conjugation

Capsular saccharides in compositions of the invention will usually be conjugated to carrier protein(s). In general, conjugation enhances the immunogenicity of saccharides as it converts them from T-independent antigens to T-dependent antigens, thus allowing priming for immunological memory. Conjugation is particularly useful for paediatric vaccines and is a well known technique [e.g. reviewed in refs. 196 and 167-175].

Preferred carrier proteins are bacteria toxins or toxoids, such as diphtheria toxoid or tetanus toxoid. The $CRM_{197}$ diphtheria toxin mutant [197-199] is particularly preferred. Other suitable carrier proteins include the *N. meningitidis* outer membrane protein [200], synthetic peptides [201,202], heat shock proteins [203,204], pertussis proteins [205,206], cytokines [207], lymphokines [207], hormones [207], growth factors [207], artificial proteins comprising multiple human CD4$^+$ T cell epitopes from various pathogen-derived antigens [208], protein D from *H. influenzae* [209,210], pneumococcal surface protein PspA [211], iron-uptake proteins [212], toxin A or B from *C. difficile* [213], etc. Preferred carriers are diphtheria toxoid, tetanus toxoid, *H. influenzae* protein D, and $CRM_{197}$.

Within a composition of the invention, it is possible to use more than one carrier protein e.g. to reduce the risk, of carrier suppression. Thus different carrier proteins can be used for different serogroups e.g. serogroup A saccharides might be conjugated to $CRM_{197}$ while serogroup C saccharides might be conjugated to tetanus toxoid. It is also possible to use more than one carrier protein for a particular saccharide antigen e.g. serogroup A saccharides might be in two groups, with some conjugated to $CRM_{197}$ and others conjugated to tetanus toxoid. In general, however, it is preferred to use the same carrier protein for all saccharides.

A single carrier protein might carry more than one saccharide antigen [214]. For example, a single carrier protein might have conjugated to it saccharides from serogroups A and C. To achieve this goal, saccharides can be mixed prior to the conjugation reaction. In general, however, it is preferred to have separate conjugates for each serogroup.

Conjugates with a saccharide:protein ratio (w/w) of between 1:5 (i.e. excess protein) and 5:1 (i.e. excess saccharide) are, preferred. Ratios between 1:2 and 5:1 are preferred, as are ratios between 1:1.25 and 1:2.5 are , more preferred. Excess carrier protein may be preferred for MenA and MenC.

Conjugates may be used in conjunction with free carrier protein [215]. When a given carrier protein is present in both free and conjugated form in a composition of the invention, the unconjugated form is preferably no more than 5% of the total amount of the carrier protein in the composition as a whole, and more preferably present at less than 2% by weight.

Any suitable conjugation reaction can be used, with any suitable linker where necessary.

The saccharide will typically be activated or functionalised prior to conjugation. Activation may involve, for example, cyanylating reagents such as CDAP (e.g. 1-cyano-4-dimethylamino pyridinium tetrafluoroborate [216,217, etc.]). Other suitable techniques use carbodiimides, hydrazides, active esters, norborane, p-nitrobenzoic acid, N-hydroxysuccinimide, S-NHS, EDC, TSTU; see also the introduction to reference 173).

Linkages via a linker group may be made using any known procedure, for example, the procedures described in references 218 and 219. One type of linkage involves reductive amination of the polysaccharide, coupling the resulting amino group with one end of an adipic acid linker group, and then coupling a protein to the other end of the adipic acid linker group [171,220,221]. Other linkers include B-propionamido [222], nitrophenyl-ethylamine [223], haloacyl halides [224], glycosidic linkages [225], 6-aminocaproic acid [226], ADH [227], $C_4$ to $C_{12}$ moieties [228] etc. As an alternative to using a linker, direct linkage can be used. Direct linkages to the protein may comprise oxidation of the polysaccharide followed by reductive amination with the protein, as described in, for example, references 229 and 230.

A process involving the introduction of amino groups into the saccharide (e.g. by replacing terminal =O groups with —NH$_2$) followed by derivatisation with an adipic diester (e.g. adipic acid N-hydroxysuccinimido diester) and reaction with carrier protein is preferred. Another preferred reaction uses CDAP activation with a protein D carrier e.g. for MenA or MenC.

After conjugation, free and conjugated saccharides can be separated. There are many suitable methods, including hydrophobic chromatography, tangential ultrafiltration, diafiltration etc. [see also refs. 231 & 232, etc.].

Where the composition of the invention includes a conjugated oligosaccharide, it is preferred that . oligosaccharide preparation precedes conjugation.

As an alternative to purification, capsular saccharides may be obtained by total or partial synthesis e.g. Hib synthesis is disclosed in ref. 233, and MenA synthesis in ref. 234.

Further and Alternative Serogroup B Polypeptide Antigens

The invention uses a composition which, after administration to a subject, is able to induce an antibody response in that subject, wherein the antibody response is protective against at least serogroup Y of meningococcus. Although NadA, 741, 936, 953 and 287 are preferred antigens for achieving this protection, other MenB polypeptide antigens which may be included in compositions of the invention (optionally in combination with one or more of the five basic antigens) include those comprising one of the following amino acid sequences: SEQ ID NO:650 from ref. 15; SEQ ID NO:878 from ref. 15; SEQ ID NO:884 from ref. 15; SEQ ID NO:4 from ref. 16; SEQ ID NO:598 from ref. 17; SEQ ID NO:818 from ref. 17; SEQ ID NO:864 from ref. 17; SEQ ID NO:866 from ref. 17; SEQ ID NO:1196 from ref. 17; SEQ ID NO;1272 from ref. 17: SEQ ID NO:1274 from ref. 17; SEQ ID NO:1640 from ref. 17; SEQ ID NO:1788 from ref. 17; SEQ ID NO:2288 from ref. 17; SEQ ID NO:2466 from ref. 17; SEQ ID NO:2554 from ref. 17; SEQ ID NO:2576 from ref. 17; SEQ ID. NO:2606 from ref. 17; SEQ ID NO:2608 from ref. 17; SEQ ID NO:2616 from ref. 17; SEQ ID NO:2668 from ref. 17; SEQ ID NO:2780 from ref. 17; SEQ ID NO:2932 from ref. 17; SEQ ID NO:2958 from ref. 17; SEQ ID NO:2970 from ref. 17; SEQ ID NO:2988 from ref. 17, or a polypeptide comprising an amino acid sequence which: (a) has 50% or more identity (e.g. 60%, 70%, 80%, 90%, 95%, 99% or more) to said sequences; and/or (b) comprises a fragment of at least n consecutive amino acids from said sequences, wherein n is 7 or more (eg. 8, 10, 12, 14, 16, 18, 20, 25, 30, 35, 40, 50, 60, 70, 80, 90, 100, 150, 200, 250 or more). Preferred fragments for (b) comprise an epitope from the relevant sequence. More than one (e.g. 2, 3, 4, 5, 6) of these polypeptides may be included.

The antigens transferrin binding protein and/or Hsf protein may also be used [235]. The NspA protein can also be used [236], preferably recombinantly expressed and purified as in reference 237.

General

The term "comprising" encompasses "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of reference 238. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is taught in reference 239.

The term "polypeptide" generally refers to a polymer of amino acid residues, and is not limited to a minimum length of the product. Thus, peptides, oligopeptides, dimers, multimers, and the like, are included within the definition. Both full-length proteins and fragments thereof are encompassed by the definition. Typically, polypeptides useful in this invention can have a maximum length suitable for the intended application. Generally, the maximum length is not critical and can easily be selected by one skilled in the art.

Polypeptides of the invention can be prepared in many ways e.g. by chemical synthesis (at least in part), by digesting longer polypeptides using proteases, by translation from RNA, by purification from cell culture (e.g. from recombinant expression), from the organism itself (e.g. after bacterial culture), from a cell line source etc. A preferred method for production of peptides <40 amino acids long involves in vitro chemical synthesis [240,241]. Solid-phase peptide synthesis is particularly preferred, such as methods based on tBoc or Fmoc [242] chemistry. Emrymatic synthesis [243] may also be used in part or in full. As an alternative to chemical synthesis, biological synthesis may be used e.g. the polypeptides may be produced by translation. This may be carried out in vitro or in vivo. Biological methods are in general restricted to the production of polypeptides based on L-amino acids, but manipulation of translation machinery (e.g. of aminoacyl tRNA molecules) can be used to allow the introduction of D-amino acids (or of other non natural amino acids, such as iodotyrosine or methylphenylalanine, azidohomoalanine, etc.) [244]. Where D-amino acids are included, however, it is preferred to use chemical synthesis. Polypeptides of the invention may have covalent modifications at the C-terminus and/or N-terminus.

Polypeptides of the invention can take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.). A purified polypeptide is separate and discrete from the whole organism in which is was expressed.

The term "nucleic acid" includes in general means.a polymeric form of nucleotides of any length, which contain deoxyribonucleotides, ribonucleotides, and/or their analogs. It includes DNA, RNA, DNA/RNA hybrids. It also includes DNA or RNA analogs, such as those containing modified backbones (e.g. peptide nucleic acids (PNAs) or phosphorothioates) or modified bases. Thus the invention includes mRNA, tRNA, rRNA, ribozymes, DNA, cDNA, recombinant nucleic acids, branched nucleic acids, plasmids, vectors, probes, primers, etc. Where nucleic acid of the. invention takes the form of RNA, it may or may not have a 5' cap.

Nucleic acids of the invention can be prepared in many ways e.g. by chemical synthesis (at least in part), by digesting longer nucleic acids using nucleases (e.g. restriction enzymes), by joining shorter nucleic acids (e.g. using ligases or polymerases), from genomic or cDNA libraries, etc.

Sequences included in nucleic acids and polypeptides to facilitate cloning or purification, etc., do not necessarily contribute to the invention and may be omitted or removed.

MODES FOR CARRYING OUT THE INVENTION

Polypeptides

ΔG287-953 hybrid polypeptide, 936-ΔG741 hybrid polypeptide and NadA$^{(NL)(C)}$ polypeptide were prepared as disclosed in reference 24. These polypeptides are encoded by sequences taken from the genomes of serogroup B strains of meningococcus.

The three polypeptides were mixed to give a combined formulation, including an aluminium hydroxide adjuvant The formulation was used to immunise mice, and bactericidal titres of immune sera were assessed against meningococcal strains in serogroups A, B, C, W135 and Y. Results against 11 strains were as follows:

| | Serogroup | | | | | | | | | |
|---|---|---|---|---|---|---|---|---|---|---|
| | B | | | A | C | W135 | Y | | | |
| Strain | 2996 | MC58 | 394/98 | 44/76 | F6124 | C11 | LPN17592 | 860800 | ES13822 | ES15085 | ES14487 |
| SBA titre | 1024 | 4096 | 1024 | 8192 | 2048 | 2048 | 512 | 65536 | 4096 | 4096 | 4096 |

Thus the mixed composition was effective in raising sera that were bactericidal against serogroup B, which is the serogroup of origin for the amino acid sequences included in the polypeptide. Titres in the same range were seen against serogroups A and C, and slightly lower titres were seen against serogroup W. Surprisingly, the highest titres were seen against strains in serogroup Y.

Moreover, the titres seen against the serogroup Y strains were equivalent to those obtained using a
tetravalent A/C/W135/Y conjugate vaccine [8]:

| | Strain | | | |
|---|---|---|---|---|
| | 860800 | ES13822 | ES15085 | ES14487 |
| Polypeptides | 65536 | 4096 | 4096 | 4096 |
| Tetravalent conjugates | 32768 | >8192 | >8192 | 4096 |

Thus, for the first time, the inventors have achieved effective immune responses against meningococcal strains from each of the pathogenic serogroups (A, B, C, W135 and Y) using polypeptide antigens and without using capsular saccharides.

It will be understood that the invention has been described by way of example only and modifications may be made whilst remaining within the scope and spirit of the invention.

REFERENCES (THE CONTENTS OF WHICH ARE HEREBY INCORPORATED BY REFERENCE)

[1] Maiden et al. (1998) *PNAS USA* 95:3140-3145.
[2] Armand et al. (1982) *J. Biol. Stand.* 10:335-339.
[3] Cadoz et al. (1985) *Vaccine* 3:340-342.
[4] Jones (2001) *Curr Opin Investig Drugs* 2:47-49.
[5] Costantino et al. (1992) *Vaccine* 10:691-8.
[6] Lieberman et al. (1996) *JAMA* 275:1499-503.
[7] WO02/058737.
[8] WO03/007985.
[9] Rennels et al. (2002) *Pediatr Infect Dis J* 21:978-979.
[10] Campbell et al. (2002) *J Infect Dis* 186:1848-1851.
[11] European patent 0939647
[12] Parkhill et al. (2000) *Nature* 404:502-506.
[13] Tettelin et al (2000) *Science* 287:1809-1815.
[14] WO00/66791.
[15] WO99/24578.
[16] WO99/36544.
[17] WO99/57280.
[18] WO00/22430.
[19] WO00/66741.
[20] Pizza et al. (2000) *Science* 287:1816-1820.
[21] WO01/64920.
[22] WO01/64922.
[23] WO03/020756.
[24] WO2004/032958.
[25] Comandticci et al. (2002) *J. Exp. Med.* 195:1445-1454.
[26] WO03/010194.
[27] WO2004/048404
[28] WO03/063766.
[29] Masignani et al. (2003) *J Exp Med* 197:789-799.
[30] WO02/09643.
[31] Katial et al. (2002) *Infect Immun* 70:702-707.
[32] WO01/52885.
[33] European patent 0301992.
[34] Bjune et al. (1991) *Lancet* 338(8775):1093-1096.
[35] Fukasawa et al. (1999) *Vaccine* 17:2951-2958.
[36] WO02/09746.
[37] Rosenqvist et al. (1998) *Dev. Biol. Stand.* 92:323-333.
[38] WO01/09350.
[39] European patent 0449958.
[40] EP-A-0996712.
[41] EP-A-0680512.
[42] WO2004/014417.
[43] WO02/062378.
[44] WO099/59625.
[45] U.S. Pat. No. 6,180,111.
[46] WO01/34642.
[47] WO03/051379.
[48] U.S. Pat. No. 6,558,677
[49] WO2004/019977
[50] WO02/062380.
[51] WO2004/002523.
[52] WO00/25811.
[53] WO2004/015099.
[54] WO03/105890.
[55] Peeters et al. (1996) *Vaccine* 14:1008-1015.
[56] Vermont et al. (2003) *Infect Immun* 71:1650-1655.
[57] Holmes et al. (1999) *Mol Biol Evol* 16:741-749.
[58] Masignani et al. (2001) *Infect Immun* 69:2580-2588.
[59] Maslanka et al. (1997) *Clin Diagn Lab Immunol* 4:156-167.
[60] Available at the website neisseria.org under the directory nm/typing/mlst/
[61] Pettersson et al. (1994) *Microb Pathog* 17(6):395-408.
[62] Welsch et al. (2002) Thirteenth International Pathogenic Neisseria Conference, Norwegian Institute of Public Health, Oslo, Norway; Sep. 1-6, 2002. *Genome-derived antigen (GNA) 2132 elicits protective serum antibodies to groups B and C Neisseria meningitidis strains.*

[63] Santos et al. (2002) Thirteenth International Pathogenic Neisseria Conference, Norwegian Institute of Public Health, Oslo, Norway; Sep. 1-6, 2002. *Serum bactericidal responses in rhesus macaques immunized with novel vaccines containing recombinant proteins derived from the genome of N. meningitidis.*
[64] WO03/009869.
[65] WO01/30390.
[66] Almeida & Alpar (1996) *J. Drug Targeting* 3:455-467.
[67] Agarwal & Mishra (1999) *Indian J Exp Biol* 37:6-16.
[68] WO00/53221.
[69] Jakobsen et al. (2002) *Infect Immun* 70:1443-1452.
[70] Wu et al. (1997) *J Infect Dis* 175:839-846.
[71] Bergquist et al. (1998) *APMS* 106:800-806.
[72] Baudner et al. (2002) *Infect Immun* 70:4785-4790.
[73] Ugozzoli et al. (2002) *J Infect Dis* 186:1358-1361.
[74] Paoletti et al. (2001) *Vaccine* 19:2118-2126.
[75] WO00/56365.
[76] Gennaro (2000) *Remington: The Science and Practice of Pharmacy.* 20th edition, ISBN: 0683306472.
[77] *Vaccine Design . . .* (1995) eds. Powell & Newman. ISBN: 030644867X. Plenum.
[78] WO00/23105.
[79] WO90/14837.
[80] U.S. Pat. No. 5,057,540.
[81] WO96/33739.
[82] EP-A-0109942.
[83] WO96/11711.
[84] WO00/07621.
[85] Barr et al (1998) *Advanced Drug Delivery Reviews* 32:247-271.
[86] Sjolanderet etal. (1998) *Advanced Drug Delivery Reviews* 32:321-338.
[87] Niikura et al. (2002) *Virology* 293:273-280.
[88] Lenz et al. (2001) *J Immunol* 166:5346-5355.
[89] Pinto et al. (2003) *J Infect Dis* 188:327-338.
[90] Gerberera/. (2001) *Virol* 75:4752-4760.
[91] WO03/024480
[92] WO03/024481
[93] Gluck et al. (2002) *Vaccine* 20:B10-B16.
[94] EP-A-0689454.
[95] Johnson et al. (1999) *Bioorg Med Chem Lett* 9:2273-2278.
[96] Evans et al. (2003) Expert Rev Vaccines 2:219-229.
[97] Meraldi et al. (2003) *Vaccine* 21:2485-2491.
[98] Pajak et al. (2003) *Vaccine* 21:836-842.
[99] Kandimalla et al. (2003) *Nucleic Acids Research* 31:2393-2400.
[100] WO02/26757.
[101] WO99/62923.
[102] Krieg (2003) *Nature Medicine* 9:831-835.
[103] McCluskie et al. (2002) *FEMS Immunology and Medical Microbiology* 32:179-185.
[104] WO98/40100.
[105] U.S. Pat. No. 6,207,646.
[106] U.S. Pat. No. 6,239,116.
[107] U.S. Pat. No. 6,429,199.
[108] kandimalla etal. (2003) *Biochemical Society Transaction* 31 (part 3):654-658.
[109] Blackwell et al. (2003) *J Immunol* 170:4061-4068.
[110] Krieg (2002) *Trends Immunol* 23:64-65.
[111] WO01/95935.
[112] Kandimalla et al. (2003) *BBRC* 306:948-953.
[113] Bhagat et al. (2003) *BBRC* 300:853-861.
[114] WO03/035836.
[115] WO95/17211.
[116] WO98/42375.
[117] Beignon et al. (2002) *Infect Immun* 70:3012-3019.
[118] Pizza et al. (2001) *Vaccine* 19:2534-2541.
[119] Pizza et al. (2000) *Int J Med Microbiol* 290:455-461.
[120] Scharton-Kersten et al. (2000) *Infect Immun* 68:5306-5313.
[121] Ryan et al. (1999) *Infect Immun* 67:6270-6280.
[122] Partidos et al. (1999) *Immunol Lett* 67:209-216.
[123] Peppoloni et al. (2003) *Expert Rev Vaccines* 2:285-293.
[124] Pine et al. (2002) *J Control Release* 85:263-270.
[125] Domenighini et al. (1995) *Mol Microbiol* 15:1165-1167.
[126] WO99/40936.
[127] WO099/44636.
[128] Singh et al. (2001) *J Cont Release* 70:267-276.
[129] WO99/27960.
[130] U.S. Pat. No. 6,090,406
[131] U.S. Pat. No. 5,916,588
[132] EP-A-0626169.
[133] WO99/52549.
[134] WO01/21207.
[135] WO01/21152.
[136] Andrianov et al. (1998) *Biomaterials* 19:109-115.
[137] Payne et al. (1998) *Adv Drug Delivery Review* 31:185-196.
[138] Stanley (2002) *Clin Exp Dermatol* 27:571-577.
[139] Jones (2003) *Curr Opin Investig Drugs* 4:214-218.
[140] WO99/11241.
[141] WO94/00153.
[142] WO98/57659.
[143] European patent applications 0835318, 0735898 and 0761231.
[144] WO96/37222; U.S. Pat. No. 6,333,036.
[145] Bell (2000) *Pediatr Infect Dis J* 19:1187-1188.
[146] Iwarson (1995) *APMIS* 103:321-326.
[147] Gerlich et al (1990) *Vaccine* 8 Suppl:S63-68 & 79-80.
[148] *Vaccines* (1988) eds. Plotkin & Mortimer. ISBN 0-7216-1946-0.
[149] Del Guidice et al. (1998) *Molecular Aspects of Medicine* 19:1-70.
[150] Gustafsson et al (1996) *N. Engl. J. Med.* 334:349-355.
[151] Rappuoli et al. (1991) *TIBTECH* 9:232-238.
[152] WO01/52885.
[153] Sutter et al. (2000) *Pediatr Clin North Am* 47:287-308.
[154] Zimmerman & Spann (1999) *Am Fam Physician* 59:113-118, 125-126.
[155] Robinson & Torres (1997) *Seminars in Immunology* 9:271-283.
[156] Donnelly et al. (1997) *Annu Rev Immunol* 15:617-648.
[157] Scott-Taylor & Dalgleish (2000) *Expert Opin Investig Drugs* 9:471-480.
[158] Apostolopoulos & Plebanski (2000) *Curr Opin Mol Ther* 2:441-447.
[159] Han (1999) *Curr Opin Mol Ther* 1:116-120.
[160] Dubensky et al. (2000) *Mol Med* 6:723-732.
[161] Robinson & Pertmer (2000) *Adv Virus Res* 55:1-74.
[162] Donnelly et al. (2000) *Am J Respir Crit Care Med* 162(4 Pt 2):S190-193.
[163] Davis (1999) *Mt. Sinai J. Med.* 66:84-90.
[164] Charalambous & Feavers (2001) *J Med Microbiol* 50:937-939.
[165] Westerink (2001) *Int Rev Immunol* 20:251-261.
[166] Grothaus et al. (2000) *Vaccine* 18:1253-1263.
[167] Lindberg (1999) *Vaccine* 17 Suppl 2:S28-36.
[168] Buttery & Moxon (2000) *J R Coll Physicians Lond* 34:163-168.

[169] Ahmad & Chapnick (1999) *Infect Dis Clin North Am* 13:113-33, vii.
[170] Goldblatt (1998) *J. Med Microbiol* 47:563-567.
[171] European patent 0477508.
[172] U.S. Pat. No. 5,306,492.
[173] WO98/42721.
[174] Dick et al. in *Conjugate Vaccines* (eds. Cruse et al.) Karger, Basel, 1989, 10:48-114.
[175] Hermanson *Bioconjugate Techniques*, Academic Press, San Diego (1996) ISBN: 0123423368.
[176] Kanra et al. (1999) *The Turkish Journal of Paediatrics* 42:421-427.
[177] Ravenscroft et al. (2000) *Dev Biol (Basel)* 103:35-47.
[178] WO97/00697.
[179] WO02/00249.
[180] Watson (2000) *Pediatr Infect Dis J* 19:331-332.
[181] Rubin (2000) *Pediatr Clin North Am* 47:269-285, v.
[182] Jedrzejas (2001) *MicrobiolMol Biol Rev* 65:187-207.
[183] Zielenera/. (2000) *Infect. Immun.* 68:1435-1440.
[184] Darkes & Plosker (2002) *Paediatr Drugs* 4:609-630.
[185] Tettelin et al. (2001) *Science* 293:498-506.
[186] Hoskins et al (2001) *J Bacteriol* 183:5709-5717.
[187] Rappuoli (2000) *Curr Opin Microbiol* 3:445-450
[188] Rappuoli (2001) *Vaccine* 19:2688-2691.
[189] Masignani et al. (2002) *Expert Opin Biol Ther* 2:895-905.
[190] Mora et al. (2003) *Drug Discov Today* 8:459-464.
[191] Wizemann et al. (2001) *Infect Immun* 69:1593-1598.
[192] Rigden et al. (2003) *Crit Rev Biochem Mol Biol* 38:143-168.
[193] WO02/22167.
[194] Ravenscroft et al. (1999) *Vaccine* 17:2802-2816.
[195] Costantino etal. (1999) *Vaccine* 17:1251-1263.
[196] Ramsay et al. (2001) *Lancet* 357(9251):195-196.
[197] Anonymous (January 2002) *Research Disclosure*, 453077.
[198] Anderson (1983) *Infect Immun* 39(1):233-238.
[199] Anderson et al. (1985) *J Clin Invest* 76(1):52-59.
[200] EP-A-0372501.
[201] EP-A-0378881.
[202] EP-A-0427347.
[203] WO93/17712
[204] WO94/03208.
[205] WO98/58668.
[206] EP-A-0471177.
[207] WO91/01146
[208] Falugi et al. (2001) *Eur J Immunol* 31:3816-3824.
[209] EP-A-0594610.
[210] WO00/56360.
[211] WO02/091998:
[212] WO01/72337
[213] WO00/61761.
[214] WO99/42130
[215] WO96/40242
[216] Lees et al. (1996) *Vaccine* 14:190-198.
[217] WO95/08348.
[218] U.S. Pat. No. 4,882,317
[219] U.S. Pat. No. 4,695,624
[220] Porro et al. (1985) *Mol Immunol* 22:907-919.s
[221] EP-A-0208375
[222] WO00/10599
[223] Gever et al. Med. Microbiol. Immunol, 165:171-288 (1979).
[224] U.S. Pat. No. 4,057,685.
[225] U.S. Pat. Nos. 4,673,574; 4,761,283; 4,808,700.
[226] U.S. Pat. No. 4,459,286.
[227] U.S. Pat. NO. 4,965,338
[228] U.S. Pat. No. 4,663,160.
[229] U.S. Pat. No. 4,761,283
[230] U.S. Pat. No. 4,356,170
[231] Lei et al. (2000) *Dev Biol (Basel)* 103:259-264.
[232] WO00/38711; U.S. Pat. No. 6,146,902.
[233] Kandil et al. (1997) *Glycoconj J* 14:13-17.
[234] Berkin et al. (2002) *Chemistry* 8:4424-4433.
[235] WO2004/014419.
[236] Martin et al. (2000) *J Biotechnol* 83:27-31.
[237] WO2004/020452.
[238] *Current Protocols in Molecular Biology* (F. M. Ausubel et al., eds., 1987) Supplement 30.
[239] Smith & Waterman (1981) *Adv. Appl. Math.* 2:482-489.
[240] Bodanszky (1993) *Principles of Peptide Synthesis* (ISBN: 0387564314).
[241] Fields et al. (1997) *Meth Enzymol* 289: *Solid-Phase Peptide Synthesis*. ISBN: 0121821900.
[242] Chan & White (2000) *Fmoc Solid Phase Peptide Synthesis*. ISBN: 0199637245.
[243] Kullmann (1987) *Enzymatic Peptide Synthesis*. ISBN: 0849368413.
[244] Ibba (1996) *Biotechnol Genet Eng Rev* 13:197-216.

The invention claimed is:

1. A method of inducing an immune response in a subject against serogroup Y of *Neisseria meningitidis*, comprising administering to the subject an immunologically effective amount of a composition comprising an aluminum adjuvant and a purified immunogenic *Neisseria meningitidis* serogroup B 741 protein having at least 95% sequence identity to the sequence of SEQ ID NO: 10, a purified immunogenic *Neisseria meningitidis* serogroup B NadA protein having at least 95% sequence identity to the sequence of SEQ ID NO: 2, a purified immunogenic *Neisseria meningitidis* serogroup B 287 protein having at least 95% sequence identity to the sequence of SEQ ID NO: 6, a purified immunogenic *Neisseria meningitidis* serogroup B 936 protein having at least 95% sequence identity to the sequence of SEQ ID NO: 4, and a purified immunogenic *Neisseria meningitidis* serogroup B 953 protein having at least 95% sequence identity to the sequence of SEQ ID NO: 5.

2. The method of claim 1, wherein an immune response against serogroup A, B, C and/or W135 of *N. meningitidis* is also induced in the subject.

3. The method of claim 1, wherein the composition further comprises a histidine buffer.

4. The method of claim 1, wherein the aluminum adjuvant comprises an aluminum phosphate.

5. The method of claim 3, wherein the aluminum phosphate is aluminum hydroxyphosphate.

6. The method of claim 4, wherein the composition further comprises a histidine buffer.

7. The method of claim 3, wherein the aluminum adjuvant is amorphous.

8. The method of claim 7, wherein the aluminum phosphate is aluminum hydroxyphosphate.

9. The method of claim 8, wherein the composition further comprises a histidine buffer.

10. The method of claim 1, wherein the composition further comprises sodium chloride at a concentration of 8-12 mg/ml.

11. The method of claim 10, wherein the aluminum adjuvant comprises an aluminum phosphate.

12. The method of claim 11, wherein the aluminum phosphate is aluminum hydroxyphosphate.

13. The method of claim 12, wherein the composition further comprises a histidine buffer.

14. The method of claim 13, wherein the composition further comprises polysorbate 80 wherein the concentration of polysorbate 80 is less than 0.01 percent.

15. The method of claim 1, wherein the composition further comprises an outer membrane vesicle preparation.

* * * * *

SEQUENCE LISTING

```
<160> NUMBER OF SEQ ID NOS: 12

<210> SEQ ID NO 1
<211> LENGTH: 350
<212> TYPE: PRT
<213> ORGANISM: Neisseria meningitidis

<400> SEQUENCE: 1

Met Lys His Phe Pro Ser Lys Val Leu Thr Thr Ala Ile Leu Ala Thr
1               5                   10                  15

Phe Cys Ser Gly Ala Leu Ala Ala Thr Asn Asp Asp Val Lys Lys
            20                  25                  30

Ala Ala Thr Val Ala Ile Ala Ala Ala Tyr Asn Asn Gly Gln Glu Ile
        35                  40                  45

Asn Gly Phe Lys Ala Gly Glu Thr Ile Tyr Asp Ile Asp Glu Asp Gly
    50                  55                  60
```

```
Thr Ile Thr Lys Lys Asp Ala Thr Ala Ala Asp Val Glu Ala Asp Asp
 65                  70                  75                  80

Phe Lys Gly Leu Gly Leu Lys Lys Val Val Thr Asn Leu Thr Lys Thr
                 85                  90                  95

Val Asn Glu Asn Lys Gln Asn Val Asp Ala Lys Val Lys Ala Ala Glu
            100                 105                 110

Ser Glu Ile Glu Lys Leu Thr Thr Lys Leu Ala Asp Thr Asp Ala Ala
            115                 120                 125

Leu Ala Asp Thr Asp Ala Ala Leu Asp Ala Thr Thr Asn Ala Leu Asn
        130                 135                 140

Lys Leu Gly Glu Asn Ile Thr Thr Phe Ala Glu Glu Thr Lys Thr Asn
145                 150                 155                 160

Ile Val Lys Ile Asp Glu Lys Leu Glu Ala Val Ala Asp Thr Val Asp
                165                 170                 175

Lys His Ala Glu Ala Phe Asn Asp Ile Ala Asp Ser Leu Asp Glu Thr
            180                 185                 190

Asn Thr Lys Ala Asp Glu Ala Val Lys Thr Ala Asn Glu Ala Lys Gln
            195                 200                 205

Thr Ala Glu Glu Thr Lys Gln Asn Val Asp Ala Lys Val Lys Ala Ala
210                 215                 220

Glu Thr Ala Ala Gly Lys Ala Glu Ala Ala Ala Gly Thr Ala Asn Thr
225                 230                 235                 240

Ala Ala Asp Lys Ala Glu Ala Val Ala Ala Lys Val Thr Asp Ile Lys
                245                 250                 255

Ala Asp Ile Ala Thr Asn Lys Asp Asn Ile Ala Lys Lys Ala Asn Ser
            260                 265                 270

Ala Asp Val Tyr Thr Arg Glu Glu Ser Asp Ser Lys Phe Val Arg Ile
            275                 280                 285

Asp Gly Leu Asn Ala Thr Thr Glu Lys Leu Asp Thr Arg Leu Ala Ser
        290                 295                 300

Ala Glu Lys Ser Ile Ala Asp His Asp Thr Arg Leu Asn Gly Leu Asp
305                 310                 315                 320

Lys Thr Val Ser Asp Leu Arg Lys Glu Thr Arg Gln Gly Leu Ala Glu
                325                 330                 335

Gln Ala Ala Leu Ser Gly Leu Phe Gln Pro Tyr Asn Val Gly
            340                 345                 350

<210> SEQ ID NO 2
<211> LENGTH: 327
<212> TYPE: PRT
<213> ORGANISM: Neisseria meningitidis

<400> SEQUENCE: 2

Ala Thr Asn Asp Asp Asp Val Lys Lys Ala Ala Thr Val Ala Ile Ala
1               5                  10                  15

Ala Ala Tyr Asn Asn Gly Gln Glu Ile Asn Gly Phe Lys Ala Gly Glu
            20                  25                  30

Thr Ile Tyr Asp Ile Asp Glu Asp Gly Thr Ile Thr Lys Lys Asp Ala
        35                  40                  45

Thr Ala Ala Asp Val Glu Ala Asp Asp Phe Lys Gly Leu Gly Leu Lys
    50                  55                  60

Lys Val Val Thr Asn Leu Thr Lys Thr Val Asn Glu Asn Lys Gln Asn
 65                  70                  75                  80

Val Asp Ala Lys Val Lys Ala Ala Glu Ser Glu Ile Glu Lys Leu Thr
                 85                  90                  95
```

Thr Lys Leu Ala Asp Thr Asp Ala Ala Leu Ala Asp Thr Asp Ala Ala
            100                 105                 110

Leu Asp Ala Thr Thr Asn Ala Leu Asn Lys Leu Gly Glu Asn Ile Thr
145                 120                 125

Thr Phe Ala Glu Glu Thr Lys Thr Asn Ile Val Lys Ile Asp Glu Lys
            130                 135                 140

Leu Glu Ala Val Ala Asp Thr Val Asp Lys His Ala Glu Ala Phe Asn
145                 150                 155                 160

Asp Ile Ala Asp Ser Leu Asp Glu Thr Asn Thr Lys Ala Asp Glu Ala
            165                 170                 175

Val Lys Thr Ala Asn Glu Ala Lys Gln Thr Ala Glu Glu Thr Lys Gln
            180                 185                 190

Asn Val Asp Ala Lys Val Lys Ala Ala Glu Thr Ala Ala Gly Lys Ala
            195                 200                 205

Glu Ala Ala Ala Gly Thr Ala Asn Thr Ala Ala Asp Lys Ala Glu Ala
210                 215                 220

Val Ala Ala Lys Val Thr Asp Ile Lys Ala Asp Ile Ala Thr Asn Lys
225                 230                 235                 240

Asp Asn Ile Ala Lys Lys Ala Asn Ser Ala Asp Val Tyr Thr Arg Glu
            245                 250                 255

Glu Ser Asp Ser Lys Phe Val Arg Ile Asp Gly Leu Asn Ala Thr Thr
            260                 265                 270

Glu Lys Leu Asp Thr Arg Leu Ala Ser Ala Glu Lys Ser Ile Ala Asp
            275                 280                 285

His Asp Thr Arg Leu Asn Gly Leu Asp Lys Thr Val Ser Asp Leu Arg
            290                 295                 300

Lys Glu Thr Arg Gln Gly Leu Ala Glu Gln Ala Ala Leu Ser Gly Leu
305                 310                 315                 320

Phe Gln Pro Tyr Asn Val Gly
            325

<210> SEQ ID NO 3
<211> LENGTH: 248
<212> TYPE: PRT
<213> ORGANISM: Neisseria meningitidis

<400> SEQUENCE: 3

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
            115                 120                 125

Gly Glu His Thr Ser Phe Asp Lys Leu Pro Glu Gly Gly Arg Ala Thr

```
                130                 135                 140
Tyr Arg Gly Thr Ala Phe Gly Ser Asp Asp Ala Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Asp Ile Lys
            180                 185                 190

Pro Asp Gly Lys Arg His Ala Val Ile Ser Gly Ser Val Leu Tyr Asn
            195                 200                 205

Gln Ala Glu Lys Gly Ser Tyr Ser Leu Gly Ile Phe Gly Gly Lys Ala
        210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245

<210> SEQ ID NO 4
<211> LENGTH: 179
<212> TYPE: PRT
<213> ORGANISM: Neisseria meningitidis

<400> SEQUENCE: 4

Val Ser Ala Val Ile Gly Ser Ala Ala Val Gly Ala Lys Ser Ala Val
1               5                   10                  15

Asp Arg Arg Thr Thr Gly Ala Gln Thr Asp Asp Asn Val Met Ala Leu
            20                  25                  30

Arg Ile Glu Thr Thr Ala Arg Ser Tyr Leu Arg Gln Asn Asn Gln Thr
        35                  40                  45

Lys Gly Tyr Thr Pro Gln Ile Ser Val Val Gly Tyr Asn Arg His Leu
    50                  55                  60

Leu Leu Leu Gly Gln Val Ala Thr Glu Gly Glu Lys Gln Phe Val Gly
65                  70                  75                  80

Gln Ile Ala Arg Ser Glu Gln Ala Ala Glu Gly Val Tyr Asn Tyr Ile
                85                  90                  95

Thr Val Ala Ser Leu Pro Arg Thr Arg Ala Gly Asp Ile Ala Gly Asp Thr
            100                 105                 110

Trp Asn Thr Ser Lys Val Arg Ala Thr Leu Leu Gly Ile Ser Pro Ala
        115                 120                 125

Thr Gln Ala Arg Val Lys Ile Val Thr Tyr Gly Asn Val Thr Tyr Val
    130                 135                 140

Met Gly Ile Leu Thr Pro Glu Glu Gln Ala Gln Ile Thr Gln Lys Val
145                 150                 155                 160

Ser Thr Thr Val Gly Val Gln Lys Val Ile Thr Leu Tyr Gln Asn Tyr
                165                 170                 175

Val Gln Arg

<210> SEQ ID NO 5
<211> LENGTH: 168
<212> TYPE: PRT
<213> ORGANISM: Neisseria meningitidis

<400> SEQUENCE: 5

Ala Thr Tyr Lys Val Asp Glu Tyr His Ala Asn Ala Arg Phe Ala Ile
1               5                   10                  15

Asp His Phe Asn Thr Ser Thr Asn Val Gly Gly Phe Tyr Gly Leu Thr
            20                  25                  30
```

```
Gly Ser Val Glu Phe Asp Gln Ala Lys Arg Asp Gly Lys Ile Asp Ile
            35                  40                  45

Thr Ile Pro Ile Ala Asn Leu Gln Ser Gly Ser Gln His Phe Thr Asp
 50                  55                  60

His Leu Lys Ser Ala Asp Ile Phe Asp Ala Ala Gln Tyr Pro Asp Ile
 65                  70                  75                  80

Arg Phe Val Ser Thr Lys Phe Asn Phe Asn Gly Lys Lys Leu Val Ser
                 85                  90                  95

Val Asp Gly Asn Leu Thr Met His Gly Lys Thr Ala Pro Val Lys Leu
            100                 105                 110

Lys Ala Glu Lys Phe Asn Cys Tyr Gln Ser Pro Met Glu Lys Thr Glu
            115                 120                 125

Val Cys Gly Gly Asp Phe Ser Thr Thr Ile Arg Thr Lys Trp Gly
130                 135                 140

Met Asp Tyr Leu Val Asn Val Gly Met Thr Lys Ser Val Arg Ile Asp
145                 150                 155                 160

Ile Gln Ile Glu Ala Ala Lys Gln
                165

<210> SEQ ID NO 6
<211> LENGTH: 464
<212> TYPE: PRT
<213> ORGANISM: Neisseria meningitidis

<400> SEQUENCE: 6

Ser Pro Asp Val Lys Ser Ala Asp Thr Leu Ser Lys Pro Ala Ala Pro
 1               5                  10                  15

Val Val Ser Glu Lys Glu Thr Glu Ala Lys Glu Asp Ala Pro Gln Ala
             20                  25                  30

Gly Ser Gln Gly Gln Gly Ala Pro Ser Ala Gln Gly Ser Gln Asp Met
            35                  40                  45

Ala Ala Val Ser Glu Glu Asn Thr Gly Asn Gly Gly Ala Val Thr Ala
 50                  55                  60

Asp Asn Pro Lys Asn Glu Asp Glu Val Ala Gln Asn Asp Met Pro Gln
 65                  70                  75                  80

Asn Ala Ala Gly Thr Asp Ser Ser Thr Pro Asn His Thr Pro Asp Pro
                 85                  90                  95

Asn Met Leu Ala Gly Asn Met Glu Asn Gln Ala Thr Asp Ala Gly Glu
            100                 105                 110

Ser Ser Gln Pro Ala Asn Gln Pro Asp Met Ala Asn Ala Ala Asp Gly
            115                 120                 125

Met Gln Gly Asp Asp Pro Ser Ala Gly Gly Gln Asn Ala Gly Asn Thr
130                 135                 140

Ala Ala Gln Gly Ala Asn Gln Ala Gly Asn Asn Gln Ala Ala Gly Ser
145                 150                 155                 160

Ser Asp Pro Ile Pro Ala Ser Asn Pro Ala Pro Ala Asn Gly Gly Ser
                165                 170                 175

Asn Phe Gly Arg Val Asp Leu Ala Asn Gly Val Leu Ile Asp Gly Pro
            180                 185                 190

Ser Gln Asn Ile Thr Leu Thr His Cys Lys Gly Asp Ser Cys Ser Gly
            195                 200                 205

Asn Asn Phe Leu Asp Glu Glu Val Gln Leu Lys Ser Glu Phe Glu Lys
            210                 215                 220

Leu Ser Asp Ala Asp Lys Ile Ser Asn Tyr Lys Lys Asp Gly Lys Asn
```

-continued

```
            225                 230                 235                 240
Asp Lys Phe Val Gly Leu Val Ala Asp Ser Val Gln Met Lys Gly Ile
                245                 250                 255
Asn Gln Tyr Ile Ile Phe Tyr Lys Pro Lys Pro Thr Ser Phe Ala Arg
                260                 265                 270
Phe Arg Arg Ser Ala Arg Ser Arg Arg Ser Leu Pro Ala Glu Met Pro
                275                 280                 285
Leu Ile Pro Val Asn Gln Ala Asp Thr Leu Ile Val Asp Gly Glu Ala
            290                 295                 300
Val Ser Leu Thr Gly His Ser Gly Asn Ile Phe Ala Pro Glu Gly Asn
305                 310                 315                 320
Tyr Arg Tyr Leu Thr Tyr Gly Ala Glu Lys Leu Pro Gly Gly Ser Tyr
                325                 330                 335
Ala Leu Arg Val Gln Gly Glu Pro Ala Lys Gly Glu Met Leu Ala Gly
                340                 345                 350
Ala Ala Val Tyr Asn Gly Glu Val Leu His Phe His Thr Glu Asn Gly
                355                 360                 365
Arg Pro Tyr Pro Thr Arg Gly Arg Phe Ala Ala Lys Val Asp Phe Gly
            370                 375                 380
Ser Lys Ser Val Asp Gly Ile Ile Asp Ser Gly Asp Asp Leu His Met
385                 390                 395                 400
Gly Thr Gln Lys Phe Lys Ala Ala Ile Asp Gly Asn Gly Phe Lys Gly
                405                 410                 415
Thr Trp Thr Glu Asn Gly Ser Gly Asp Val Ser Gly Lys Phe Tyr Gly
                420                 425                 430
Pro Ala Gly Glu Glu Val Ala Gly Lys Tyr Ser Tyr Arg Pro Thr Asp
            435                 440                 445
Ala Glu Lys Gly Gly Phe Gly Val Phe Ala Gly Lys Lys Glu Gln Asp
            450                 455                 460

<210> SEQ ID NO 7
<211> LENGTH: 644
<212> TYPE: PRT
<213> ORGANISM: Neisseria meningitidis

<400> SEQUENCE: 7

Met Ala Ser Pro Asp Val Lys Ser Ala Asp Thr Leu Ser Lys Pro Ala
1               5                   10                  15
Ala Pro Val Val Ser Glu Lys Glu Thr Glu Ala Lys Glu Asp Ala Pro
                20                  25                  30
Gln Ala Gly Ser Gln Gly Gln Gly Ala Pro Ser Ala Gln Gly Gly Gln
            35                  40                  45
Asp Met Ala Ala Val Ser Glu Glu Asn Thr Gly Asn Gly Gly Ala Ala
        50                  55                  60
Ala Thr Asp Lys Pro Lys Asn Glu Asp Glu Gly Ala Gln Asn Asp Met
65                  70                  75                  80
Pro Gln Asn Ala Ala Asp Thr Asp Ser Leu Thr Pro Asn His Thr Pro
                85                  90                  95
Ala Ser Asn Met Pro Ala Gly Asn Met Glu Asn Gln Ala Pro Asp Ala
                100                 105                 110
Gly Glu Ser Glu Gln Pro Ala Asn Gln Pro Asp Met Ala Asn Thr Ala
            115                 120                 125
Asp Gly Met Gln Gly Asp Asp Pro Ser Ala Gly Gly Glu Asn Ala Gly
        130                 135                 140
```

-continued

```
Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
            165                 170                 175

Gly Gly Asp Phe Gly Arg Thr Asn Val Gly Asn Ser Val Val Ile Asp
        180                 185                 190

Gly Pro Ser Gln Asn Ile Thr Leu Thr His Cys Lys Gly Asp Ser Cys
        195                 200                 205

Ser Gly Asn Asn Phe Leu Asp Glu Glu Val Gln Leu Lys Ser Glu Phe
    210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
            260                 265                 270

Pro Thr Ser Phe Ala Arg Phe Arg Arg Ser Ala Arg Ser Arg Arg Ser
        275                 280                 285

Leu Pro Ala Glu Met Pro Leu Ile Pro Val Asn Gln Ala Asp Thr Leu
290                 295                 300

Ile Val Asp Gly Glu Ala Val Ser Leu Thr Gly His Ser Gly Asn Ile
305                 310                 315                 320

Phe Ala Pro Glu Gly Asn Tyr Arg Tyr Leu Thr Tyr Gly Ala Glu Lys
                325                 330                 335

Leu Pro Gly Gly Ser Tyr Ala Leu Arg Val Gln Gly Glu Pro Ser Lys
            340                 345                 350

Gly Glu Met Leu Ala Gly Thr Ala Val Tyr Asn Gly Glu Val Leu His
        355                 360                 365

Phe His Thr Glu Asn Gly Arg Pro Ser Pro Ser Arg Gly Arg Phe Ala
        370                 375                 380

Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                405                 410                 415

Gly Asn Gly Phe Lys Gly Thr Trp Thr Glu Asn Gly Gly Asp Val
            420                 425                 430

Ser Gly Lys Phe Tyr Gly Pro Ala Gly Glu Glu Val Ala Gly Lys Tyr
        435                 440                 445

Ser Tyr Arg Pro Thr Asp Ala Glu Lys Gly Gly Phe Gly Val Phe Ala
450                 455                 460

Gly Lys Lys Glu Gln Asp Gly Ser Gly Gly Gly Ala Thr Tyr Lys
465                 470                 475                 480

Val Asp Glu Tyr His Ala Asn Ala Arg Phe Ala Ile Asp His Phe Asn
                485                 490                 495

Thr Ser Thr Asn Val Gly Gly Phe Tyr Gly Leu Thr Gly Ser Val Glu
            500                 505                 510

Phe Asp Gln Ala Lys Arg Asp Gly Lys Ile Asp Ile Thr Ile Pro Val
        515                 520                 525

Ala Asn Leu Gln Ser Gly Ser Gln His Phe Thr Asp His Leu Lys Ser
        530                 535                 540

Ala Asp Ile Phe Asp Ala Ala Gln Tyr Pro Asp Ile Arg Phe Val Ser
545                 550                 555                 560

Thr Lys Phe Asn Phe Asn Gly Lys Lys Leu Val Ser Val Asp Gly Asn
```

```
                        565                 570                 575

Leu Thr Met His Gly Lys Thr Ala Pro Val Lys Leu Lys Ala Glu Lys
                580                 585                 590

Phe Asn Cys Tyr Gln Ser Pro Met Ala Lys Thr Glu Val Cys Gly Gly
                595                 600                 605

Asp Phe Ser Thr Thr Ile Asp Arg Thr Lys Trp Gly Val Asp Tyr Leu
        610                 615                 620

Val Asn Val Gly Met Thr Lys Ser Val Arg Ile Asp Ile Gln Ile Glu
625                 630                 635                 640

Ala Ala Lys Gln
                645

<210> SEQ ID NO 8
<211> LENGTH: 434
<212> TYPE: PRT
<213> ORGANISM: Neisseria meningitidis

<400> SEQUENCE: 8

Met Val Ser Ala Val Ile Gly Ser Ala Ala Val Gly Ala Lys Ser Ala
1               5                   10                  15

Val Asp Arg Arg Thr Thr Gly Ala Gln Thr Asp Asp Asn Val Met Ala
                20                  25                  30

Leu Arg Ile Glu Thr Thr Ala Arg Ser Tyr Leu Arg Gln Asn Asn Gln
            35                  40                  45

Thr Lys Gly Tyr Thr Pro Gln Ile Ser Val Val Gly Tyr Asn Arg His
        50                  55                  60

Leu Leu Leu Leu Gly Gln Val Ala Thr Glu Gly Glu Lys Gln Phe Val
65                  70                  75                  80

Gly Gln Ile Ala Arg Ser Glu Gln Ala Ala Glu Gly Val Tyr Asn Tyr
                85                  90                  95

Ile Thr Val Ala Ser Leu Pro Arg Thr Ala Gly Asp Ile Ala Gly Asp
                100                 105                 110

Thr Trp Asn Thr Ser Lys Val Arg Ala Thr Leu Leu Gly Ile Ser Pro
            115                 120                 125

Ala Thr Gln Ala Arg Val Lys Ile Val Thr Tyr Gly Asn Val Thr Tyr
        130                 135                 140

Val Met Gly Ile Leu Thr Pro Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg Gly Ser Gly Gly Gly Val Ala Ala Asp Ile Gly
                180                 185                 190

Ala Gly Leu Ala Asp Ala Leu Thr Ala Pro Leu Asp His Lys Asp Lys
            195                 200                 205

Gly Leu Gln Ser Leu Thr Leu Asp Gln Ser Val Arg Lys Asn Glu Lys
        210                 215                 220

Leu Lys Leu Ala Ala Gln Gly Ala Glu Lys Thr Tyr Gly Asn Gly Asp
225                 230                 235                 240

Ser Leu Asn Thr Gly Lys Leu Lys Asn Asp Lys Val Ser Arg Phe Asp
                245                 250                 255

Phe Ile Arg Gln Ile Glu Val Asp Gly Gln Leu Ile Thr Leu Glu Ser
                260                 265                 270

Gly Glu Phe Gln Val Tyr Lys Gln Ser His Ser Ala Leu Thr Ala Phe
            275                 280                 285
```

```
Gln Thr Glu Gln Ile Gln Asp Ser Glu His Ser Gly Lys Met Val Ala
    290                 295                 300
Lys Arg Gln Phe Arg Ile Gly Asp Ile Ala Gly Glu His Thr Ser Phe
305                 310                 315                 320
Asp Lys Leu Pro Glu Gly Gly Arg Ala Thr Tyr Arg Gly Thr Ala Phe
                325                 330                 335
Gly Ser Asp Asp Ala Gly Gly Lys Leu Thr Tyr Thr Ile Asp Phe Ala
            340                 345                 350
Ala Lys Gln Gly Asn Gly Lys Ile Glu His Leu Lys Ser Pro Glu Leu
        355                 360                 365
Asn Val Asp Leu Ala Ala Ala Asp Ile Lys Pro Asp Gly Lys Arg His
    370                 375                 380
Ala Val Ile Ser Gly Ser Val Leu Tyr Asn Gln Ala Glu Lys Gly Ser
385                 390                 395                 400
Tyr Ser Leu Gly Ile Phe Gly Gly Lys Ala Gln Glu Val Ala Gly Ser
                405                 410                 415
Ala Glu Val Lys Thr Val Asn Gly Ile Arg His Ile Gly Leu Ala Ala
            420                 425                 430
Lys Gln

<210> SEQ ID NO 9
<211> LENGTH: 6
<212> TYPE: PRT
<213> ORGANISM: Artificial Sequence
<220> FEATURE:
<223> OTHER INFORMATION: Linker

<400> SEQUENCE: 9

Gly Ser Gly Gly Gly Gly
1               5

<210> SEQ ID NO 10
<211> LENGTH: 255
<212> TYPE: PRT
<213> ORGANISM: Neisseria meningitidis

<400> SEQUENCE: 10

Cys Ser Ser Gly Gly Gly Val Ala Ala Asp Ile Gly Ala Gly Leu
1               5                   10                  15
Ala Asp Ala Leu Thr Ala Pro Leu Asp His Lys Asp Lys Gly Leu Gln
                20                  25                  30
Ser Leu Thr Leu Asp Gln Ser Val Arg Lys Asn Glu Lys Leu Lys Leu
            35                  40                  45
Ala Ala Gln Gly Ala Glu Lys Thr Tyr Gly Asn Gly Asp Ser Leu Asn
        50                  55                  60
Thr Gly Lys Leu Lys Asn Asp Lys Val Ser Arg Phe Asp Phe Ile Arg
65                  70                  75                  80
Gln Ile Glu Val Asp Gly Gln Leu Ile Thr Leu Glu Ser Gly Glu Phe
                85                  90                  95
Gln Val Tyr Lys Gln Ser His Ser Ala Leu Thr Ala Phe Gln Thr Glu
                100                 105                 110
Gln Ile Gln Asp Ser Glu His Ser Gly Lys Met Val Ala Lys Arg Gln
            115                 120                 125
Phe Arg Ile Gly Asp Ile Ala Gly Glu His Thr Ser Phe Asp Lys Leu
        130                 135                 140
Pro Glu Gly Gly Arg Ala Thr Tyr Arg Gly Thr Ala Phe Gly Ser Asp
145                 150                 155                 160
```

```
Asp Ala Gly Gly Lys Leu Thr Tyr Thr Ile Asp Phe Ala Ala Lys Gln
            165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
            195                 200                 205

Ser Gly Ser Val Leu Tyr Asn Gln Ala Glu Lys Gly Ser Tyr Ser Leu
            210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
            245                 250                 255

<210> SEQ ID NO 11
<211> LENGTH: 254
<212> TYPE: PRT
<213> ORGANISM: Neisseria meningitidis

<400> SEQUENCE: 11

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250

<210> SEQ ID NO 12
<211> LENGTH: 262
<212> TYPE: PRT
```

-continued

```
<213> ORGANISM: Neisseria meningitidis

<400> SEQUENCE: 12

Cys Ser Ser Gly Gly Gly Gly Ser Gly Gly Gly Gly Val Ala Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Pro Gln Asn
        35                  40                  45

Gly Thr Leu Thr Leu Ser Ala Gln Gly Ala Glu Lys Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asn His Ser
            100                 105                 110

Ala Val Val Ala Leu Gln Ile Glu Lys Ile Asn Asn Pro Asp Lys Thr
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Pro Asn Gly Arg Leu His Tyr Ser
                165                 170                 175

Ile Asp Phe Thr Lys Lys Gln Gly Tyr Gly Arg Ile Glu His Leu Lys
            180                 185                 190

Thr Leu Glu Gln Asn Val Glu Leu Ala Ala Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
            260
```